(12) United States Patent
Combe et al.

(10) Patent No.: US 11,661,613 B2
(45) Date of Patent: May 30, 2023

(54) METHODS AND MATERIALS FOR THE BIOSYNTHESIS OF HYDROXY FATTY ACID ANIONS AND/OR DERIVATIVES THEREOF AND/OR COMPOUNDS RELATED THERETO

(71) Applicant: INV Nylon Chemicals Americas, LLC, Wilmington, DE (US)

(72) Inventors: Jonathan Paul Combe, Redcar (GB); Alexander Brett Foster, Redcar (GB); Arghya Barman, Redcar (GB)

(73) Assignee: INV NYLON CHEMICALS AMERICAS, LLC, Wilmington, DE (US)

( * ) Notice: Subject to any disclaimer, the term of this patent is extended or adjusted under 35 U.S.C. 154(b) by 140 days.

(21) Appl. No.: 16/264,739

(22) Filed: Feb. 1, 2019

(65) Prior Publication Data

US 2019/0233849 A1    Aug. 1, 2019

Related U.S. Application Data

(60) Provisional application No. 62/624,910, filed on Feb. 1, 2018.

(51) Int. Cl.
| | |
|---|---|
| *C12P 7/42* | (2006.01) |
| *C12N 9/10* | (2006.01) |
| *C12N 9/90* | (2006.01) |
| *C12N 1/20* | (2006.01) |
| *C12R 1/01* | (2006.01) |

(52) U.S. Cl.
CPC ............... *C12P 7/42* (2013.01); *C12N 1/205* (2021.05); *C12N 9/1029* (2013.01); *C12N 9/90* (2013.01); *C12R 2001/01* (2021.05); *C12Y 203/01009* (2013.01)

(58) Field of Classification Search
CPC ......... C12P 7/42; C12N 1/205; C12N 9/1029; C12Y 203/01009
See application file for complete search history.

(56) References Cited

U.S. PATENT DOCUMENTS

| | | | |
|---|---|---|---|
| 2011/0151530 A1 | 6/2011 | Soucaille et al. | 435/146 |
| 2011/0171702 A1 | 7/2011 | Reinecke et al. | 435/135 |
| 2015/0267231 A1 | 9/2015 | Haas et al. | C12P 7/52 |
| 2016/0208293 A1 | 7/2016 | Burgard et al. | C12P 7/42 |
| 2017/0101631 A1 | 4/2017 | Koepke et al. | C12N 9/1217 |
| 2017/0145441 A1 | 5/2017 | Conradie | C12P 5/007 |
| 2018/0100160 A1 | 4/2018 | Bawdon et al. | |

FOREIGN PATENT DOCUMENTS

| | | |
|---|---|---|
| WO | WO 2007/110394 | 10/2007 |
| WO | 2014044674 | 3/2014 |

OTHER PUBLICATIONS

Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostablity. 2018. Structure. 26, 1474-1485. (Year: 2018).*
Kizer L et al. Application of Functional Genomics to Pathway Optimization for Increased Isoprenoid Production. Applied and Environmental Microbiology. 2008. vol. 74, No. 10. p. 3229-3241. (Year: 2008).*
Prather KLJ et al. De novo biosynthetic pathways: Rational design of microbial chemical factories. Current Opinion in Biotechnology. 2008. 19:468-474 (Year: 2008).*
Kegg Enzyme 5.4.99.2. p. 1. Obtained on Jan. 26, 2021 (Year: 2021).*
GenBank WP_046128597.1. 2015. Methylmalonyl-CoA mutase. p. 1 (Year: 2015).*
GenBank THIL_CUPNH. 2016. GenBank. p. 1-5. (Year: 2016).*
International Search Report and Written Opinion in PCT/US209/013211 dated Apr. 24, 2019.
International Preliminary Report on Patentability in PCT/US209/013211 dated Aug. 4, 2019.
Byrd et al. "Bacterial control of Agromyces ramosus in soil" Can J Microbiol 1985 31:1157-1163.
Campanello et al. "Switch I-dependent allosteric signaling in a G-protein chaperone-$B_{12}$ enzyme complex" Journal of Biological Chemistry 2017 292:17617-17625.
Hoefel et al. "Reaction engineering studies for the production of 2-hydroxyisobutyric acid with recombinant Cupriavidus necator H 16" Appl Microbiol Biotechnol. 2010 88:477-484.
Lopes Ferreira et al. "Genes involved in the methyl tert-butyl ether (MTBE) metabolic pathway of *Mycobacterium austroafricanum* IFP 2012" Microbiology 2006 152:1361-1374.
Makkar, N.S. and Casida, L.E. "*Cupriavidus necator* gen. nov., sp. nov.; a Nonobligate Bacterial Predator of Bacteria in Soil" Int. J. of Systematic Bacteriology 1987 37:323-326.
Náray-Szabó, G and Mika, L. "Conservative evolution and industrial metabolism in Green Chemistry" Green Chem. 2018 20:2171-2191.
Przybylski et al. "Exploiting mixtures of H2, CO2, and O2 for improved production of methacrylate precursor 2-hydroxyisobutyric acid by engineered Cupriavidus necator strains" 2015 99:2131-2145.
Przybylski et al. "Synthesis of the building block 2-hydroxyisobutyrate from fructose and butyrate by Cupriavidus necator H16" Appl Microbiol Biotechnol 2013 97:8875-8885.
Rohde et al. "Production of 2-Hydroxyisobutyric Acid from Methanol by Methylobacterium extorquens AM1 Expressing (R)-3-Hydroxybutyryl Coenzyme A-Isomerizing Enzymes" 2017 83:1-18.
Rohwerder, T. and Muller, R.H. "Biosynthesis of 2-hydroxyisobutyric acid (2-HIBA) from renewable carbon" Microb. Cell Factories 2010 9:1-10.
Schlegel, H.G. and Vollbrecht, D. "Formation of the Dehydrogenases for Lactate, Ethanol and Butanediol in the Strictly Aerobic Bacterium Alcaligenes eutrophus" Journal of General Microbiology 1980 117:475-481.

(Continued)

*Primary Examiner* — Paul J Holland

(57) ABSTRACT

Methods and materials for the production of hydroxy fatty acid anions, including 2-hydroxyisobutyric acid (2-HIBA), and/or derivatives thereof and compounds related thereto are provided. Also provided are products produced in accordance with these methods and materials.

2 Claims, 4 Drawing Sheets

Specification includes a Sequence Listing.

(56) References Cited

OTHER PUBLICATIONS

Sillman, C. E. and Casida, L. E. "Isolation of nonobligate bacterial predators of bacteria from soil" Can J Microbiol 1986 32:760-762.

Steinbüchel, A. and Schlegel, H.G. "Excretion of pyruvate by mutants of Alcaligenes eutrophus, which are impaired in the accumulation of poly(β-hydroxybutyric acid) (PHB), under conditions permitting synthesis of PHB" Appl Microbiol Biotechnol 1989 31:168-175.

Takahashi-Iñiguez et al. "Role of vitamin B12 on methylmalonyl-CoA mutase activity" Science B 2012 vol. 13:423-437.

Vollbrecht et al. "Excretion of metabolites by hydrogen bacteria. 1. Autotrophic and heterotrophic fermentations" Eur J Appl Microbiol Biotechnol 1978 6:145-155.

Vollbrecht et al. "Excretion of metabolites by hydrogen bacteria. 4. Respiration rate-dependent formation of primary metabolites and of poly-3-hydroxybutanoate" European J. Appl. Microbiol. Biotechnol. 1979 7:267-276.

Vollbrecht, D. and Schlegel, H.G. "Excretion of metabolites by hydrogen bacteria. 2. Influences of aeration, pH, temperature, and age of cells" European J. Appl. Microbiol. Biotechnol. 1978 6:157-166.

Vollbrecht, D. and Schlegel, H.G. "Excretion of metabolites by hydrogen bacteria. 3. D(−)-3-Hydroxybutanoate" European J. Appl. Microbiol. Biotechnol. 1979 7:259-266.

Weichler et al. "Thermophilic Coenzyme B12-Dependent Acyl Coenzyme A (CoA) Mutase from Kyrpidia tusciae DSM 2912 Preferentially Catalyzes Isomerization of (R)-3-Hydroxybutyryl-CoA and 2-Hydroxyisobutyryl-CoA" Appl Environ Microbiol 2015 81:4564-4572.

Yaneva et al. "Bacterial acyl-CoA mutase specifically catalyzes coenzyme B12-dependent isomerization of 2-hydroxyisobutyryl-CoA and (S)-3-hydroxybutyryl-CoA" J Biol Chem 2012 287:15502-11551.

Zeph, L.E. and Casida, L.E. "Gram-negative versus gram-positive (actinomycete) nonobligate bacterial predators of bacteria in soil" Applied and Environmental Microbiology 1986 52:819-823.

\* cited by examiner

METHODS AND MATERIALS FOR THE BIOSYNTHESIS OF HYDROXY FATTY ACID ANIONS AND/OR DERIVATIVES THEREOF AND/OR COMPOUNDS RELATED THERETO

This patent application claims the benefit of priority from U.S. Provisional Application Ser. No. 62/624,910, filed Feb. 1, 2018, the contents of which are hereby incorporated by reference in their entirety.

FIELD

The present invention relates to biosynthetic methods and materials for the production of hydroxy fatty acid anions, such as 2-hydroxyisobutyric acid (2-HIBA), and/or derivatives thereof and/or compounds related thereto. The present invention also relates to products biosynthesized or otherwise encompassed by these methods and materials.

Replacement of traditional chemical production processes relying on, for example fossil fuels and/or potentially toxic chemicals, with environmentally friendly (e.g., green chemicals) and/or "cleantech" solutions is being considered, including work to identify suitable building blocks suitable for use in the manufacturing of such chemicals. See, "Conservative evolution and industrial metabolism in Green Chemistry", Green Chem., 2018, 20, 2171-2191.

2-HIBA has been identified as a potential building block used in industry, as practically all compounds having an isobutene structure are obtainable by relatively straightforward chemical conversions (Rohde et al. Appl Environ Microbiol. 2017 17; 83(3) e02622-16; Rohwerder T. & Muller R. H. Microb. Cell Factories 2010 9:13). For example, 2-HIBA is a precursor of 2,3-dihydroxy-methylproprionate, 2-propanol and methacrylate. Methacrylate, also referred to as methacrylic acid, is a large volume chemical used widely in resins, plastics, rubber and denture materials produced routinely with toxic chemicals including hydrogen cyanide, formaldehyde and methacrolein.

Enzymatic production of 2-HIBA from 2-methyl-2-hydroxypropanol via hydroxybutyraldehyde dehydrogenase has been described by Lopes Ferreira et al. (Microbiology 2006 152:1361-74).

WO 2007/110394 discloses a method for enzymatic conversion of 3-hydroxybutyric acid into 2-HIBA with enzyme extracts from a microorganism expressing 3-hydroxycarboxylate-CoA mutase enzymatic activity or by culturing on media a microorganism expressing 3-hydroxycarboxylate-CoA mutase enzymatic activity.

Published U.S. Patent Application No. 20110151530 discloses a method for the biological preparation of 2-HIBA, including a fermentation method with microorganisms reportedly modified to produce 2-HIBA from renewable resources such as acetyl-CoA.

A *C. necator* strain deficient in poly(3-hydroxybutyrate) (PHB) synthesis has been used to produce gram per liter quantities of 2-HIBA via heterologous expression of a (S)-3-hydroxybutyryl CoA mutase from *Aquincola tertiaricarbonis* L108 (HCM) according to some reports (Hoefel et al. Appl Microbiol Biotechnol. 2010 88(2):477-84; Przybylski et al. Appl Microbiol Biotechnol. 2013 97(20): 8875-85).

Hoefel et al. 2010, supra, reportedly attempted to utilize the polyhydroxyalkanoate (PHA) pathway for the production of 2-HIBA via recombinant expression of the *A. tertiaricarbonis* L108 3-hydroxybutyryl-CoA mutase (HCM) in *C. necator* H16 PHB-4, a strain carrying a phaC1 point mutation that abolished PHA synthase activity in the cell. However, the resulting 2-HIBA productivity of ca. 80 µmol $g^{-1}$ $h^{-1}$ during a fed-batch fermentation run with fructose as the only carbon source was approximately 6-10 times lower than native PHA productivities under similar fermentation conditions (reviewed by Przybylski et al. 2013, supra).

It was subsequently reported that the *A. tertiaricarbonis* 3-hydroxybutyryl-CoA mutase (HCM) specifically catalyzes the isomerization of (S)-3-hydroxybutyryl-CoA enantiomer to 2-hydroxyisobutyryl-CoA in an in vitro enzyme assay (Yaneva et al. J Biol Chem. 2012 287(19):15502-11). Accordingly, *A. tertiaricarbonis* HCM is unlikely to be directly channeling flux from the PHA pathway which utilizes (R)-3-hydroxybutyryl-CoA. Instead, the enzyme was predicted to utilize the (S)-3-hydroxybutyryl-CoA pool produced either from central metabolism, via acetyl-CoA and acetoacetyl-CoA, or the fatty acid degradation pathway (FIG. 1). This was determined by comparing the performance of the 2-HIBA production strain in a fed-batch fermentation experiment with fructose or butyrate as the main carbon source (Przybylski et al. 2013, supra). 2-HIBA productivities were approximately 2 times higher with butyrate as the carbon source compared to fructose, which is consistent with the S-enantiospecificity of the *A. tertiaricarbonis* enzyme, as butyrate directly feeds into (S)-3-hydroxybutyryl-CoA synthesis via the fatty acid β-oxidation pathway.

The inferior performance of the 2-HIBA pathway via (S)-3-hydroxybutyryl-CoA, compared to the native PHA pathway, was illustrated by a $CO_2/H_2$ gas fermentation experiment with the same *C. necator* 2-HIBA strain (Przybylski et al. Appl Microbiol Biotechnol. 2015 99(5):2131-45). 2-HIBA productivities peaked during the nutrient limitation phase of the fermentation run at 155 µmol $g^{-1}$ $h^{-1}$, compared with >1 mM $g^{-1}$ $h^{-1}$ for PHA. A significant product inhibition of 2-HIBA synthesis was reportedly observed at 2-HIBA concentrations of 1 g/L and above (Przybylski et al. 2015, supra).

Since the original work on the *A. tertiaricarbonis* HCM, two R-enantioselective 3-hydroxybutyryl-CoA mutases (RCMs) have been identified in *Kyrpidia tusciae* (Weichler et al. Appl Environ Microbiol. 2015 81(14):4564-72) and *Bacillus massiliosenegalensis* (Rohde et al. 2017 supra). Both enzymes have successfully channeled flux from the PHA overflow metabolism of the methylotroph *Methylobacterium extorquens* AM1, producing upwards of 43 µmol $g^{-1}$ $h^{-1}$ of 2-HIBA in a fed batch fermentation run wherein methanol was utilized as a carbon source (Rohde et al. 2017, supra).

Biosynthetic materials and methods, including organisms having increased production of hydroxy fatty acid anions such as 2-HIBA, and/or derivatives thereof and/or compounds related thereto, are needed.

SUMMARY OF THE INVENTION

An aspect of the present invention relates to a process for the biosynthesis of hydroxy fatty acid anions, such as 2-HIBA, and/or derivatives thereof and/or compounds related thereto. In one aspect, the process comprises obtaining an organism capable of producing 2-HIBA and derivatives and compounds related thereto, altering the organism, and producing more 2-HIBA and derivatives and compounds related thereto in the altered organism as compared to the unaltered organism.

In one nonlimiting embodiment of the present invention, the organism is *C. necator* or an organism with one or more properties similar thereto. In one nonlimiting embodiment, the organism is altered to express an RCM or a polypeptide having the activity of an RCM. In one nonlimiting embodiment, the RCM comprises *K. tusciae* RcmA (SEQ ID NO:9), *K. tusciae* RcmB (SEQ ID NO:11), *B. massiliosenegalensis* RcmA (SEQ ID NO:15) or *B. massiliosenegalensis* RcmB (SEQ ID NO:17) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 9, 11, 15 or 17, or a functional fragment thereof. In one nonlimiting embodiment, the RCM is encoded by a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18), or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18, or a functional fragment thereof.

In one nonlimiting embodiment, the organism is further altered to express acetoacetyl-CoA transferase, PhaA. In one nonlimiting embodiment the acetoacetyl-CoA transferase, PhaA is *C. necator* acetoacetyl-CoA transferase, phaA (SEQ ID NO:19) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 19. In one nonlimiting embodiment, the acetoacetyl-CoA transferase, PhaA is encoded by a nucleic acid sequence comprising SEQ ID NO:20 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof.

In one nonlimiting embodiment, the nucleic acid sequence is codon optimized for *C. necator*.

In one nonlimiting embodiment, the organism is further altered to abolish PHA synthase activity.

Another aspect of the present invention relates to an organism altered to produce more 2-HIBA and/or derivatives and compounds related thereto as compared to the unaltered organism. In one nonlimiting embodiment, the organism is *C. necator* or an organism with properties similar thereto. In one nonlimiting embodiment, the organism is altered to express RCM. In one nonlimiting embodiment, the RCM comprises *K. tusciae* RcmA (SEQ ID NO:9), *K. tusciae* RcmB (SEQ ID NO:11), *B. massiliosenegalensis* RcmA (SEQ ID NO:15) or *B. massiliosenegalensis* RcmB (SEQ ID NO:17) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 9, 11, 15 or 17 or a functional fragment thereof. In one nonlimiting embodiment, the RCM is encoded by a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18 or a functional fragment thereof.

In one nonlimiting embodiment, the organism is further altered to express acetoacetyl-CoA transferase, PhaA. In one nonlimiting embodiment the acetoacetyl-CoA transferase, PhaA is *C. necator* acetoacetyl-CoA transferase, PhaA (SEQ ID NO:19) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 19. In one nonlimiting embodiment, the acetoacetyl-CoA transferase, PhaA is encoded by a nucleic acid sequence comprising SEQ ID NO:20 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof.

In one nonlimiting embodiment, the nucleic acid sequence is codon optimized for *C. necator*.

In one nonlimiting embodiment, the organism is further altered to abolish PHA synthase activity.

In one nonlimiting embodiment, the organism is altered to express, overexpress, not express or express less of one or more molecules depicted in FIG. 1. In one nonlimiting embodiment, the molecule(s) comprise a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence corresponding to a molecule(s) depicted in FIG. 1, or a functional fragment thereof.

Another aspect of the present invention relates to bio-derived, bio-based, or fermentation-derived products produced from any of the methods and/or altered organisms disclosed herein. Such products include compositions comprising at least one bio-derived, bio-based, or fermentation-derived compound or any combination thereof, as well as bio-derived, bio-based, or fermentation-derived polymers comprising these bio-derived, bio-based, or fermentation-derived compositions or compounds; bio-derived, bio-based, or fermentation-derived resins, plastics and/or rubbers comprising the bio-derived, bio-based, or fermentation-derived compositions or compounds or any combination thereof or the bio-derived, bio-based, or fermentation-derived polymers or any combination thereof; molded substances obtained by molding the bio-derived, bio-based, or fermentation-derived polymers or the bio-derived, bio-based, or fermentation-derived resins, plastics or rubbers, or any combination thereof; bio-derived, bio-based, or fermentation-derived formulations comprising the bio-derived, bio-based, or fermentation-derived compositions or compounds, polymers or resins, plastics or rubbers, or the bio-derived, bio-based, or fermentation-derived molded substances, or any combination thereof; and bio-derived, bio-based, or fermentation-derived semi-solids or non-semi-solid streams comprising the bio-derived, bio-based, or fermentation-derived compositions or compounds, polymers, resins, plastics or rubbers, molded substances or formulations, or any combination thereof.

Another aspect of the present invention relates to a bio-derived, bio-based or fermentation derived product biosynthesized in accordance with the exemplary central metabolism depicted in FIG. 1.

Another aspect of the present invention relates to exogenous genetic molecules of the altered organisms disclosed herein. In one nonlimiting embodiment, the exogenous genetic molecule comprises a codon optimized nucleic acid sequence. In one nonlimiting embodiment, the nucleic acid sequence is codon optimized for *C. necator*. In one nonlimiting embodiment, the exogenous genetic molecule comprises a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18 or a functional fragment thereof. In one nonlimiting embodiment, the exogenous genetic molecule comprises a nucleic acid sequence comprising *C. necator* acetoacetyl-CoA transferase, phaA (SEQ ID NO:20) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof. Additional nonlimiting examples of exogenous genetic molecules include expression constructs of, for example, RCM and/or acetoacetyl-CoA transferase and synthetic or non-synthetic isolated operons of, for example RCM and/or acetoacetyl-CoA transferase, or fragments thereof.

Yet another aspect of the present invention relates to means and processes for use of these means for biosynthesis of 2-HIBA, and/or derivatives thereof and/or compounds related thereto.

DETAILED DESCRIPTION

Figure 1:
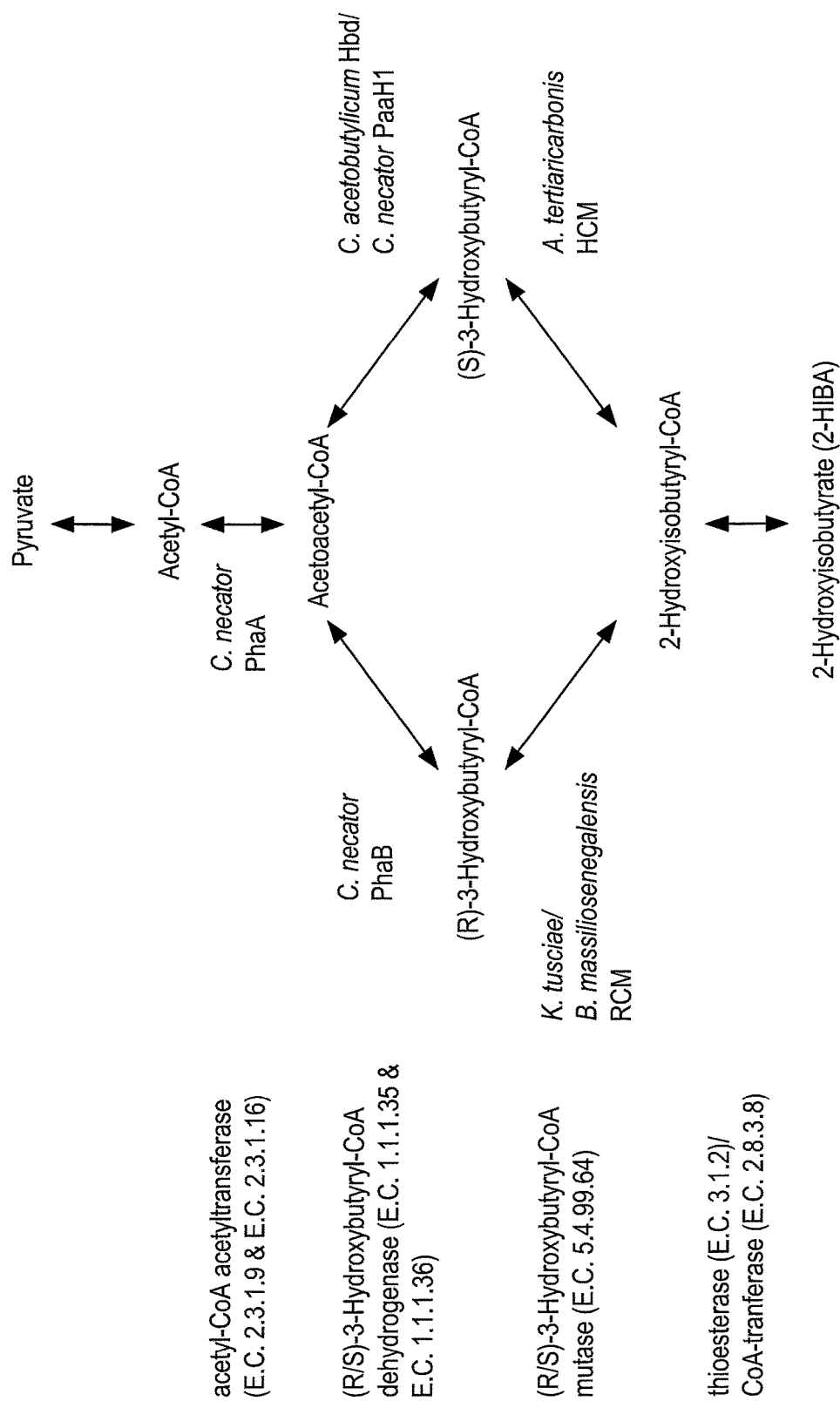
FIG. 1 is an exemplary schematic of the production of 2-hydroxyisobutyric acid (2-HIBA) from central metabolism via (R) or (S)-3-Hydroxybutyryl-CoA mutase (RCM or HCM, respectively).

The present invention provides processes for biosynthesis of hydroxy fatty acid anions, including 2-hydroxyisobutyric acid (2-HIBA) and/or derivatives thereof and/or compounds related thereto, and organisms altered to increase biosynthesis of 2-HIBA and derivatives and compounds related thereto and organisms related thereto, exogenous genetic molecules of these altered organisms, and bio-derived, bio-based, or fermentation-derived products biosynthesized or otherwise produced by any of these methods and/or altered organisms.

(S)-3-hydroxybutyryl-CoA mutase (HCM) has been disclosed to isomerize (S)-3-hydroxybutyryl-CoA, produced from the β-oxidation of fatty acids or from fructose metabolism via acetyl CoA and acetoacetyl CoA, to 2-hydroxybutyryl-CoA. The CoA moiety is subsequently cleaved by a thioesterase or CoA transferase to release 2-HIBA. The inventors herein have now found that the R-enantioselective 3-hydroxybutyryl-CoA mutases (RCM) provide a higher flux route to 2-HIBA via the acetoacetyl-CoA reductase activity (phaB) of the polyhydroxyalkanoate pathway (see FIG. 1). Accordingly, organisms altered to express RCM can be used in accordance with the present invention in methods for, inter alia, biosynthesizing higher levels of 2-HIBA and compounds related thereto.

The R/S 3-Hydroxybutyryl-CoA mutases (E.C. 5.4.99.64) are members of a wider family of acyl-CoA mutases that use a highly reactive free radical, generated from a vitamin $B_{12}$ cofactor, to catalyze the 1,2 re-arrangement of the carboxylic acid skeleton of acyl-CoA ester substrates (reviewed by Takahashi-Iñiguez et al. Science B 2012 vol. 13, 6: 423-37). The acyl-CoA mutases consist of a holoenzyme with separate substrate-binding and vitamin B12-binding domains arranged in a variety of topological configurations with a G-protein chaperone of the meaB/meaH family. For the 3-hydroxybutyryl-CoA mutases, the holoenzyme is formed by the heterodimerization of a larger substrate-binding subunit and a smaller vitamin B12-binding subunit, with the MeaB chaperone forming a larger complex consisting of 2 holoenzymes and 1 meaB molecule (Campanello et al., Journal of Biological Chemistry. 2017 292:17617-17625). The meaB/meaH chaperone performs house-keeping functions by gating the insertion of the vitamin $B_{12}$ 5' adeoxyadenosylcobalamin (AdoCbl) cofactor into the holoenzyme and the reactivation of the enzyme when the AdoCbl cofactor has been inactivated by the occasional loss of the 5′-deoxyadenosine moiety during the catalytic cycle.

For purposes of the present invention, by "2-hydroxyisobutyric acid (2-HIBA) and derivatives and compounds related thereto" it is meant to encompass 2-hydroxybutyrate, 2-hydroxy-2-methylpropionic acid, 2-methyllactic acid, alpha-hydroxybutyrate and α-hydroxybutyrate as well as compounds derived from the same substrates and/or enzymatic reactions as 2-HIBA and having similar chemical structure as well as structural analogs wherein one or more substituents of 2-HIBA are replaced with alternative substituents.

For purposes of the present invention, by "higher levels of 2-HIBA" it is meant that the altered organisms and methods of the present invention are capable of producing increased levels of 2-HIBA and derivatives and compounds related thereto as compared to organisms heterologously expressing HCM or RCM and/or the same organism without alteration. In one nonlimiting embodiment, levels are increased by 2-fold or higher.

For compounds containing carboxylic acid groups such as organic monoacids, hydroxyacids, amino acids and dicarboxylic acids, these compounds may be formed or converted to their ionic salt form when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate and/or bicarbonate, sodium hydroxide, ammonia and the like. The salt can be isolated as is from the system as the salt or converted to the free acid by reducing the pH to, for example, below the lowest pKa through addition of acid or treatment with an acidic ion exchange resin.

For compounds containing amine groups such as but not limited to organic amines, amino acids and diamine, these compounds may be formed or converted to their ionic salt form by addition of an acidic proton to the amine to form the ammonium salt, formed with inorganic acids such as hydrochloric acid, hydrobromic acid, sulfuric acid, nitric acid, phosphoric acid, and the like; or formed with organic acids such as carbonic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4′-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid or muconic acid, and the like. The salt can be isolated as is from the system as a salt or converted to the free amine by raising the pH to, for example, above the highest pKa through addition of base or treatment with a basic ion exchange resin. Acceptable inorganic bases are known in the art and include aluminum hydroxide, calcium hydroxide, potassium hydroxide, sodium carbonate or bicarbonate, sodium hydroxide, and the like.

For compounds containing both amine groups and carboxylic acid groups such as but not limited to aminoacids, these compounds may be formed or converted to their ionic salt form by either 1) acid addition salts, formed with inorganic acids such as hydrochloric acid, hydrobromic acid, sulfuric acid, nitric acid, phosphoric acid, and the like; or formed with organic acids such as carbonic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4′-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. Acceptable inorganic bases include aluminum hydroxide, calcium hydroxide, potassium hydroxide, sodium carbonate and/or bicarbonate, sodium hydroxide, and the like, or 2) when an acidic proton present in the parent compound either is replaced by a metal ion, e.g., an alkali metal ion, an alkaline earth ion, or an aluminum ion; or coordinates with an organic base. Acceptable organic bases are known in the art and include ethanolamine, diethanolamine, triethanolamine, trimethylamine, N-methylglucamine, and the like. Acceptable inorganic bases are known in the art and include aluminum hydroxide, calcium hydroxide, potassium hydroxide, sodium carbonate, sodium hydroxide, ammonia and the like. The salt can be isolated as is from the system or converted to the free acid by reducing the pH to, for example, below the pKa through addition of acid or treatment with an acidic ion exchange resin. In one or more aspects of the invention, it is understood that the amino acid salt can be isolated as: i. at low pH, as the ammonium (salt)-free acid form; ii. at high pH, as the amine-carboxylic acid salt form; and/or iii. at neutral or midrange pH, as the free-amine acid form or zwitterion form.

In the process for biosynthesis of 2-HIBA and derivatives and compounds related thereto of the present invention, an organism capable of producing 2-HIBA and derivatives and compounds related thereto is obtained. The organism is then altered to produce more 2-HIBA and derivatives and compounds related thereto in the altered organism as compared to the unaltered organism.

In one nonlimiting embodiment, the organism is *Cupriavidus necator* (*C. necator*) or an organism with properties similar thereto. A nonlimiting embodiment of the organism is set for at lgcstandards-atcc with the extension .org/products/all/17699.aspx?geo_country=gb#generalinformation of the world wide web.

*C. necator* (previously called *Hydrogenomonas eutrophus, Alcaligenes eutropha, Ralstonia eutropha*, and *Wautersia eutropha*) is a Gram-negative, flagellated soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. *C. necator* does not naturally contain genes for RCM and therefore does not express this enzyme. Additional properties of *C. necator* include microaerophilicity, copper resistance (Makar, N. S. & Casida, L. E. Int. J. of Systematic Bacteriology 1987 37(4): 323-326), bacterial predation (Makar, N. S. & Casida, L. E. Int. J. of Systematic Bacteriology 1987 37(4): 323-326), bacterial predation (Byrd et al. Can J Microbiol 1985 31:1157-1163; Sillman, C. E. & Casida, L. E. Can J Microbiol 1986 32:760-762; Zeph, L. E. & Casida, L. E. Applied and Environmental Microbiology 1986 52(4):819-823) and polyhydroxybutyrate (PHB) synthesis. In addition, the cells have been reported to be capable of both aerobic and nitrate dependent anaerobic growth. A nonlimiting example of a *C. necator* organism useful in the present invention is a *C. necator* of the H16 strain. In one nonlimiting embodiment, a *C. necator* host of the H16 strain with at least a portion of the phaC1AB1 gene locus knocked out (ΔphaCAB), as described in U.S. patent application Ser. No. 15/717,216, teachings of which are incorporated herein by reference, is used.

In another nonlimiting embodiment, the organism altered in the process of the present invention has one or more of the above-mentioned properties of *Cupriavidus necator*.

In another nonlimiting embodiment, the organism is selected from non-pathogenic members of the genera *Ralstonia, Wautersia, Cupriavidus, Alcaligenes, Burkholderia* or *Pandoraea*.

For the process of the present invention, the organism is altered to express RCM.

In one nonlimiting embodiment, the RCM comprises *K. tusciae* RcmA (SEQ ID NO:9), *K. tusciae* RcmB (SEQ ID NO:11), *B. massiliosenegalensis* RcmA (SEQ ID NO:15) or *B. massiliosenegalensis* RcmB (SEQ ID NO:17) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 9, 11, 15 or 17 or a functional fragment thereof.

In one nonlimiting embodiment, the RCM is encoded by a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18 or a functional fragment thereof.

In one nonlimiting embodiment, the RCM is classified in E.C. 5.4.99.64.

In one nonlimiting embodiment, the organism is further altered to express acetoacetyl-CoA transferase, PhaA. In one nonlimiting embodiment the acetoacetyl-CoA transferase, PhaA is *C. necator* acetoacetyl-CoA transferase, PhaA (SEQ ID NO:19) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 19. In one nonlimiting embodiment, the acetoacetyl-CoA transferase, PhaA is encoded by a nucleic acid sequence comprising SEQ ID NO:20 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof.

In one nonlimiting embodiment, the phaA is classified in E.C. 2.3.1.9 or E.C. 2.3.1.16.

In one nonlimiting embodiment, the nucleic acid sequence or sequences are codon optimized for *C. necator*.

In one nonlimiting embodiment, the organism is further altered to abolish PHA synthase activity.

In the process of the present invention, the altered organism is then subjected to conditions wherein 2-HIBA and derivatives and compounds related thereto are produced.

In the process described herein, a fermentation strategy can be used that entails anaerobic, micro-aerobic or aerobic cultivation. A fermentation strategy can entail nutrient limitation such as nitrogen limitation or phosphate limitation or oxygen limitation.

Under conditions of nutrient limitation a phenomenon known as overflow metabolism (also known as energy spilling, uncoupling or spillage) occurs in many bacteria (Russell, 2007). In growth conditions in which there is a relative excess of carbon source and other nutrients (e.g. phosphorous, nitrogen and/or oxygen) are limiting cell growth, overflow metabolism results in the use of this excess energy (or carbon), not for biomass formation but for the excretion of metabolites, typically organic acids. In *Cupriavidus necator* a modified form of overflow metabolism occurs in which excess carbon is sunk intracellularly into the storage carbohydrate polyhydroxybutyrate (PHB). In strains of *C. necator* which are deficient in PHB synthesis this overflow metabolism can result in the production of extracellular overflow metabolites. The range of metabolites that have been detected in PHB deficient *C. necator* strains include acetate, acetone, butanoate, cis-aconitate, citrate, ethanol, fumarate, 3-hydroxybutanoate, propan-2-ol, malate, methanol, 2-methyl-propanoate, 2-methyl-butanoate, 3-methyl-butanoate, 2-oxoglutarate, meso-2,3-butanediol, acetoin, DL-2,3-butanediol, 2-methylpropan-1-ol, propan-1-ol, lactate 2-oxo-3-methylbutanoate, 2-oxo-3-methylpentanoate, propanoate, succinate, formic acid and pyruvate. The range of overflow metabolites produced in a particular fermentation can depend upon the limitation applied (e.g. nitrogen, phosphate, oxygen), the extent of the limitation, and the carbon source provided (Schlegel, H. G. & Vollbrecht, D. Journal of General Microbiology 1980 117:475-481; Steinbüchel, A. & Schlegel, H. G. Appl Microbiol Biotechnol 1989 31: 168; Vollbrecht et al. Eur J Appl Microbiol Biotechnol 1978 6:145-155; Vollbrecht et al. European J. Appl. Microbiol. Biotechnol. 1979 7: 267; Vollbrecht, D. & Schlegel, H. G. European J. Appl. Microbiol. Biotechnol. 1978 6: 157; Vollbrecht, D. & Schlegel, H. G. European J. Appl. Microbiol. Biotechnol. 1979 7: 259).

Applying a suitable nutrient limitation in defined fermentation conditions can thus result in an increase in the flux through a particular metabolic node. The application of this knowledge to *C. necator* strains genetically modified to produce desired chemical products via the same metabolic node can result in increased production of the desired product.

A cell retention strategy using a ceramic hollow fiber membrane can be employed to achieve and maintain a high cell density during fermentation. The principal carbon source fed to the fermentation can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) a caustic wash waste stream from cyclohexane oxidation processes or waste stream from a chemical industry such as, but not limited to a carbon black industry or a hydrogen-refining industry, or petrochemical industry.

In one nonlimiting embodiment, at least one of the enzymatic conversions of the 2-HIBA production method comprises gas fermentation within the recombinant *Cupriavidus necator* host, or member of the genera *Ralstonia, Wautersia, Alcaligenes, Burkholderia* and *Pandoraea*, and other recombinant organism having one or more of the above-mentioned properties of *Cupriavidus necator*. In one nonlimiting embodiment, the gas fermentation may comprise at least one of natural gas, syngas, $CO_2/H_2$, $CO$, $H_2$, $O_2$, methanol, ethanol, non-volatile residue, caustic wash from cyclohexane oxidation processes, or waste stream from a chemical industry such as, but not limited to a carbon black industry or a hydrogen-refining industry, or petrochemical industry. In one nonlimiting embodiment, the gas fermentation comprises $CO$, $H_2$, $CO_2$, $O_2$ or $CO_2/H_2$.

In one nonlimiting embodiment, the conditions comprise batch fermentation run with fructose as the predominant, or in some cases the only carbon source.

The methods of the present invention may further comprise recovering produced hydroxy fatty acid anions, such as 2-HIBA or derivatives or compounds related thereto. Once produced, any method can be used to isolate the 2-HIBA or compounds related thereto.

The present invention also provides altered organisms capable of biosynthesizing increased amounts of hydroxy fatty acid anions, such as 2-HIBA and derivatives and compounds related thereto as compared to the unaltered organism. In one nonlimiting embodiment, the altered organism of the present invention is a genetically engineered strain of *Cupriavidus necator* capable of producing 2-HIBA and derivatives and compounds related thereto. In another nonlimiting embodiment, the organism to be altered is selected from non-pathogenic members of the genera *Ralstonia, Wautersia, Alcaligenes, Cupriavidus, Burkholderia* and *Pandoraea*, and other organisms having one or more of the above-mentioned properties of *Cupriavidus necator*. In one nonlimiting embodiment, the present invention relates to a substantially pure culture of the altered organism capable of producing 2-HIBA and derivatives and compounds related thereto via a RCM pathway.

As used herein, a "substantially pure culture" of an altered organism is a culture of that microorganism in which less than about 40% (i.e., less than about 35%; 30%; 25%; 20%; 15%; 10%; 5%; 2%; 1%; 0.5%; 0.25%; 0.1%; 0.01%; 0.001%; 0.0001%; or even less) of the total number of viable cells in the culture are viable cells other than the altered microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of altered microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

Altered organisms of the present invention comprise at least one genome-integrated synthetic operon encoding an enzyme.

In one nonlimiting embodiment, the altered organism is produced by integration of a synthetic operon encoding RCM into the host genome.

In one nonlimiting embodiment, the RCM comprises *K. tusciae* RcmA (SEQ ID NO:9), *K. tusciae* RcmB (SEQ ID NO:11), *B. massiliosenegalensis* RcmA (SEQ ID NO:15) or *B. massiliosenegalensis* RcmB (SEQ ID NO:17) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO: 9, 11, 15 or 17 or a functional fragment thereof.

In one nonlimiting embodiment, the RCM is encoded by a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18 or a functional fragment thereof.

In one nonlimiting embodiment, the organism is further altered to express acetoacetyl-CoA transferase, PhaA. In one nonlimiting embodiment the acetoacetyl-CoA transferase, PhaA is *C. necator* acetoacetyl-CoA transferase, PhaA (SEQ ID NO:19) or a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to an amino acid sequence set forth in SEQ ID NO:19. In one nonlimiting embodiment, the acetoacetyl-CoA transferase, PhaA is encoded by a nucleic acid sequence comprising SEQ ID NO:20 or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof.

In one nonlimiting embodiment, the nucleic acid sequence or sequences are codon optimized for *C. necator*.

In one nonlimiting embodiment, the altered organism is produced by integration of a synthetic operon comprising SEQ ID NO: 10, 12, 16 or 18.

In one nonlimiting embodiment, the altered organism further comprises a synthetic operon comprising SEQ ID NO:20.

The percent identity (and/or homology) between two amino acid sequences as disclosed herein can be determined as follows. First, the amino acid sequences are aligned using the BLAST 2 Sequences (Bl2seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods and organisms disclosed herein. The term "functional fragment" as used herein refers to a peptide or fragment of a polypeptide or a nucleic acid sequence fragment encoding a peptide fragment of a polypeptide that has at least about 25% (e.g., at least: 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

Functional fragments may range in length from about 10% up to 99% (inclusive of all percentages in between) of the original full-length sequence.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagluttanin (HA), glutathione-S-transferase (GST), or maltose binding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Endogenous genes of the organisms altered for use in the present invention also can be disrupted to prevent the formation of undesirable metabolites or prevent the loss of intermediates in the pathway through other enzymes acting on such intermediates. In one embodiment, the organism used in the present invention is further altered to abolish PHA synthase activity.

Thus, as described herein, altered organisms can include exogenous nucleic acids encoding RCM, as described herein, as well as modifications to endogenous genes.

The term "exogenous" as used herein with reference to a nucleic acid (or a protein) and an organism refers to a nucleic acid that does not occur in (and cannot be obtained from) a cell of that particular type as it is found in nature or a protein encoded by such a nucleic acid. Thus, a non-naturally-occurring nucleic acid is considered to be exogenous to an organism or host once utilized by or in the organism or host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is a non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be a non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

The present invention also provides exogenous genetic molecules of the nonnaturally occurring organisms disclosed herein such as, but not limited to, codon optimized nucleic acid sequences, expression constructs and/or synthetic operons.

In one nonlimiting embodiment, the exogenous genetic molecule comprises a codon optimized nucleic acid sequence optimized for *C. necator*. In one nonlimiting embodiment, the exogenous genetic molecule comprises a nucleic acid sequence comprising *K. tusciae* RcmA (SEQ ID NO:10), *K. tusciae* RcmB (SEQ ID NO:12), *B. massiliosenegalensis* RcmA (SEQ ID NO:16) or *B. massiliosenegalensis* RcmB (SEQ ID NO:18) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 10, 12, 16 or 18 or a functional fragment thereof. In one nonlimiting embodiment, the exogenous genetic molecule comprises a nucleic acid sequence comprising *C. necator* acetoacetyl-CoA transferase, phaA (SEQ ID NO:20) or a nucleic acid sequence encoding a polypeptide with similar enzymatic activities exhibiting at least about 50%, 60%, 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 20 or a functional fragment thereof.

In another nonlimiting embodiment, the exogenous genetic molecule comprises an RCM expression construct.

In another nonlimiting embodiment, the exogenous genetic molecule comprises a synthetic operon encoding RCM and/or acetoacetyl-CoA transferase, PhaA1.

Also provided by the present invention are 2-HIBA and derivatives and compounds related thereto bioderived from an altered organism according to any of methods described herein.

Further, the present invention relates to means and processes for use of these means for biosynthesis of 2-HIBA and derivatives and compounds related thereto. Nonlimiting examples of such means include altered organisms and exogenous genetic molecules as described herein as well as any of the molecules as depicted in FIG. 1.

In addition, the present invention provides bio-derived, bio-based, or fermentation-derived products produced using the methods and/or altered organisms disclosed herein. In one nonlimiting embodiment, a bio-derived, bio-based or fermentation derived product is produced in accordance with the exemplary central metabolism depicted in FIG. 1. Examples of such products include, but are not limited to, compositions comprising at least one bio-derived, bio-based, or fermentation-derived compound or any combination thereof, as well as polymers, resins, plastics and rubbers, molded substances, formulations and semi-solid or non-semi-solid streams comprising one or more of the bio-derived, bio-based, or fermentation-derived compounds or compositions, combinations or products thereof.

The utility of RCM in increasing biosynthesis of 2-HIBA in genetically engineered strains of *Cupriavidus necator* was evaluated against the previously characterized *A. tertiaricarbonis* HCM enzyme. To abolish PHA synthase activity, two *C. necator* H16 base strains were created incorporating deletions of either the whole phaC1AB1 operon or just the phaC1 ORF. Though both strains were deficient in PHA synthesis, the ΔphaC1 strain retained the full complement of genes (phaB1, phaB2 and phaB3) coding for the (R) 3-hydroxybutyryl-CoA dehydrogenase activity within *C. necator*, whereas the ΔphaC1AB1 deletion removed the most abundantly expressed (R)-3-hydroxybutyryl-CoA dehydrogenase gene, phaB1. The ΔphaC1 strain was therefore expected to maximize flux for the *K. tusciae* and *B. massiliosenegalensis* RCM enzymes, whilst the ΔphaC1AB1 strain was expected to channel more flux through the HCM-dependent pathway by reducing (R)-3-hydroxybutyryl-CoA side-product formation.

Figure 2:
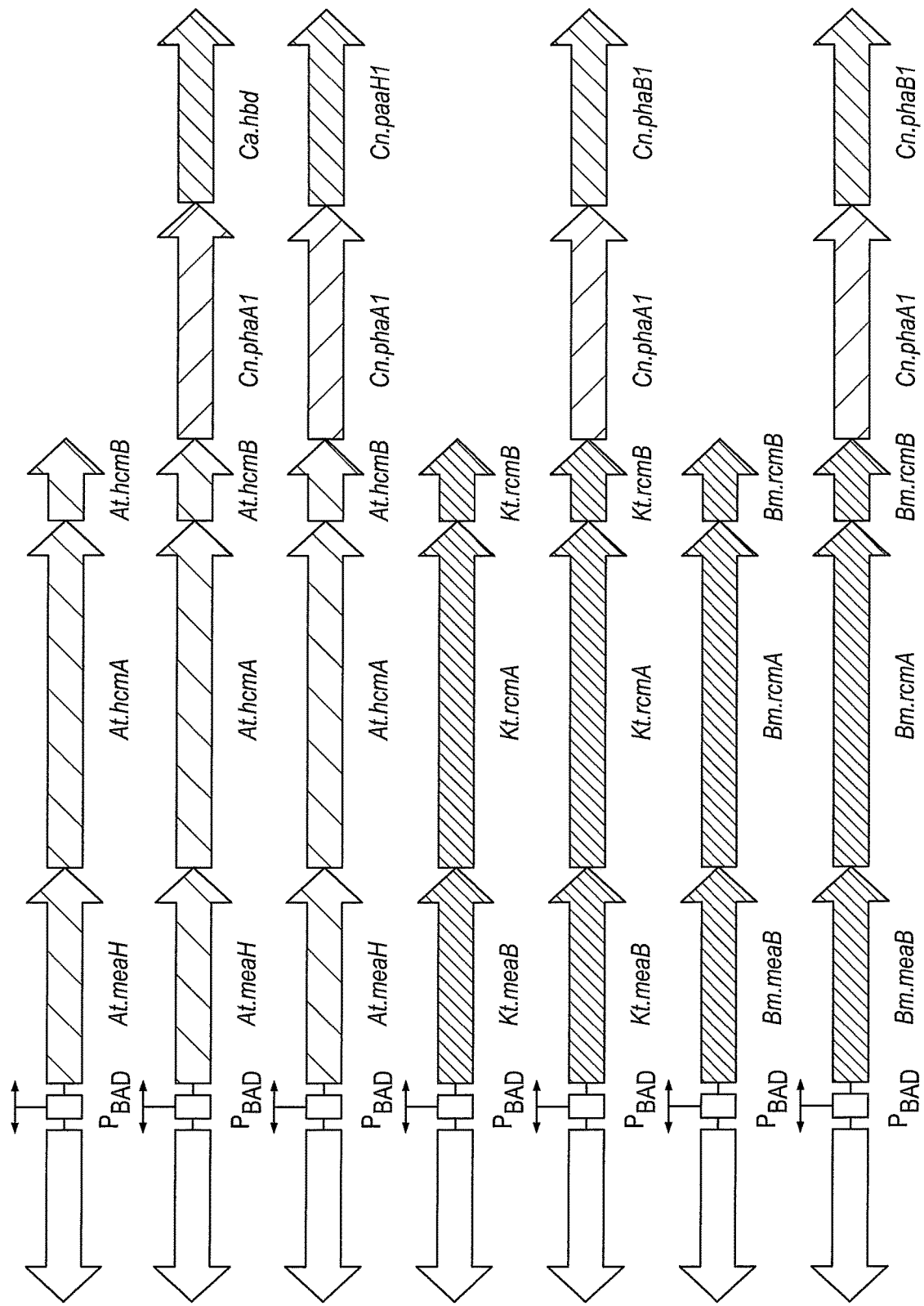
FIG. 2 shows genetic constructs for the production of 2-HIBA by either the (S)-3-hydroxybutyryl-CoA or the (R)-3-hydroxybutyryl-CoA-dependent pathway in *C. necator*. At.meaH represents *A. tertiaricarbonis* meaB G-protein chaperone (AFK77667) (SEQ ID NO: 1 and 2); At.hcmA represents *A. tertiaricarbonis* hcmA large HCM subunit (AFK77668) (SEQ ID NO: 3 and 4); At.hcmB represents *A. tertiaricarbonis* hcmB small HCM subunit (AFK77665) (SEQ ID NO: 5 and 6); Cn.phaA1 represents *C. necator* H16 phaA1 (WP_010810132) (SEQ ID NO: 19 and 20); Ca.hbd represents *C. acetobutylicum* hbd (WP_010965995) (SEQ ID NO:23 and 24); Cn.paaH1 represents *C. necator* H16 paaH1 (WP_010814882) (SEQ ID NO: 21 and 22); Kt.meaB represents *K. tusciae* meaB G-protein chaperone (WP_013074529) (SEQ ID NO: 7 and 8); Kt.rcmA represents *K. tusciae* rcmA large RCM subunit (WP_013074530) (SEQ ID NO: 9 and 10); Kt.rcmB represents *K. tusciae* rcmB small RCM subunit (WP_013074531) (SEQ ID NO: 11 and 12); CnphaB1 represents *C. necator* H16 phaB1 (WP_010810131) (SEQ ID NO: 25 and 26); Bm.meaB represents *B. massiliosenegalensis* meaB G-protein chaperone (WP_019152978) (SEQ ID NO: 13 and 14); Bm.rcmA represents *B. massiliosenegalensis* rcmA large RCM subunit (WP_019152977) (SEQ ID NO: 15 and 16); and Bm.rcmB represents *B. massiliosenegalensis* rcmB small RCM subunit (WP_019152976) (SEQ ID NO: 17 and 18).

To make a direct comparison between the RCM and HCM-dependent pathways in *C. necator*, a series of arabinose-inducible expression constructs were assembled encoding the two subunits for each of the 3-hydroxybutyryl-mutases tested and their respective meaB G-protein chaperones. Synthetic operons were cloned into a pBBR1-based plasmid. In addition to these basic constructs expressing the core (R/S)-3-hydroxybutyryl-CoA mutase activity, larger operons were assembled that also expressed *C. necator* acetoacetyl-CoA transferase, phaA, and either an (S) or (R)-3-hydroxybutyryl-CoA dehydrogenase to maximize HCM/RCM substrate availability (FIG. 2). All 7 HCM/RCM expression constructs were introduced into the ΔphaC1 *C. necator* strain by electroporation. The 3 HCM constructs were also introduced into the ΔphaC1AB1 knock-out strain, to enable a direct comparison of the two *C. necator* genetic backgrounds and establish whether more flux can be channeled through the HCM-dependent pathway by the deletion of phaB1.

Figure 3:
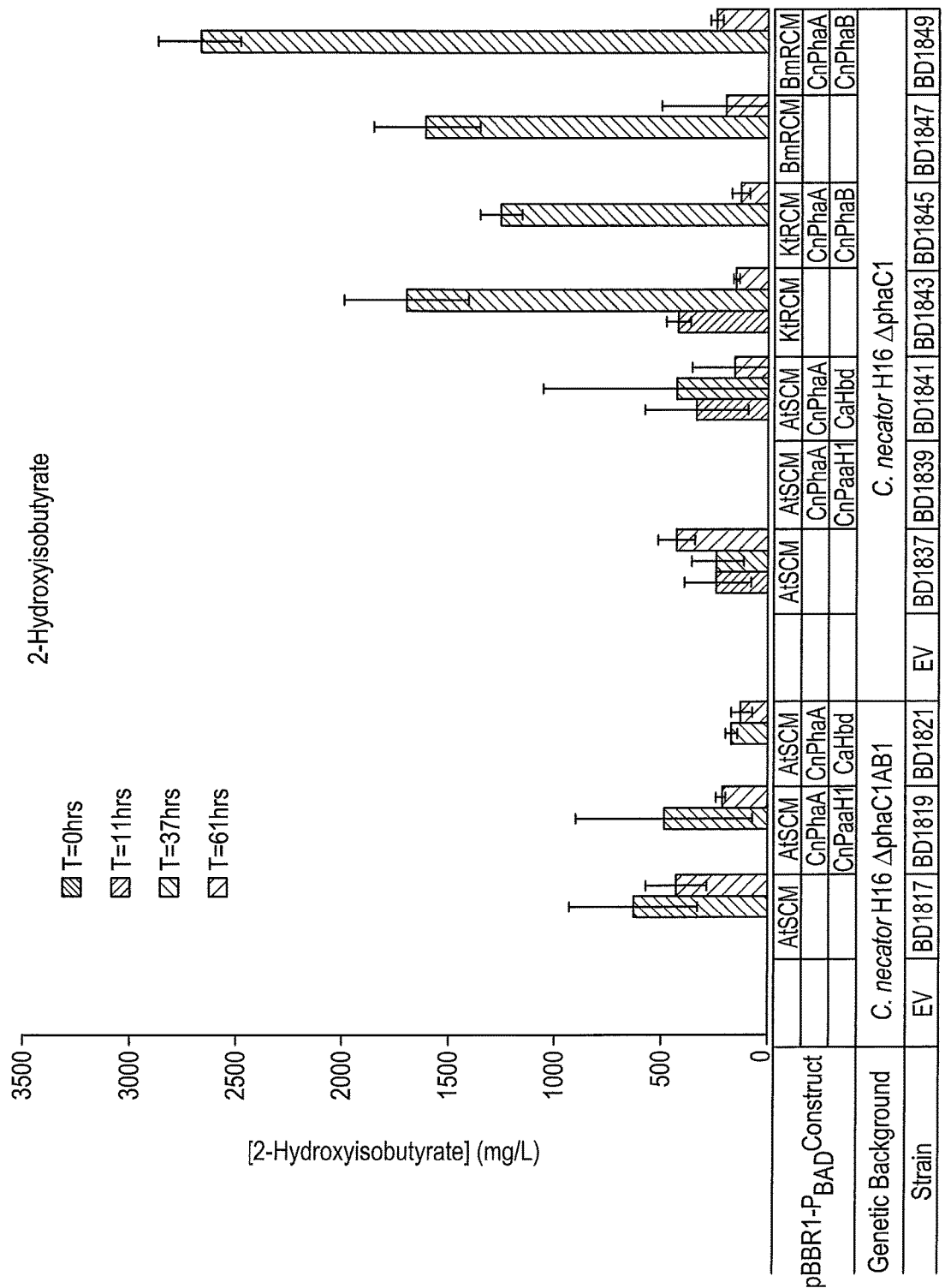
FIG. 3 shows production of 2-HIBA from *C. necator* strains expressing either *A. tertiaricarbonis* (S)-3-hydroxybutyryl-CoA mutase or *K. tusciae*/*B. massiliosenegalensis* (R)-3-hydroxybutyryl-CoA mutase during growth in fed-batch cultures. 2-HIBA titers were measured in the culture supernatant at induction (T=0 hours) and 11 (T=11 hours), 37 (T=37 hours) and 61 hours (T=61 hours) following induction. Error bars represent standard deviation of the mean. EV, empty vector control; AtHCM, At.meaH-At.hcmA-At.hcmB ORFS expressing *A. tertiaricarbonis* HCM; KtRCM, Kt.meaB-Kt.rcmA-Kt.rcmB ORFS expressing *K. tusciae* RCM; BmRCM, Bm.meaB-Bm.rcmA-Bm.rcmB ORFS expressing *B. massiliosenegalensis* RCM; CnPhaA, *C. necator* PhaA1; CnPaaH1, *C. necator* (S) 3-Hydroxybutyryl-CoA dehydrogenase, PaaH1; CaHbd, *Clostridium acetobutylicum* (S) 3-Hydroxybutyryl-CoA dehydrogenase, hbd; CnPhaB, *C. necator* (R) 3-Hydroxybutyryl-CoA dehydrogenase, phaB1.

Ten *C. necator* strains were evaluated during a fed-batch fermentation run with fructose as the only carbon source. Vitamin B12 was added at a concentration of 0.1 g/L. The strains were cultured in batch mode for 12 hours, HCM/RCM operon expression was then induced by the addition of 0.3% w/v arabinose and the strains were run in fed-batch mode for approximately 36 hours. The media feed was then switched off and the strains were cultured for a further 24 hours under starvation conditions. Maximum 2-HIBA titers were observed after 37 hours of arabinose induction, at the very end of the fed-batch phase, with the four RCM strains producing 1.5 g/L to 2.7 g/L 2-HIBA, compared with a peak titers of ca. 0.5 g/L for the HCM constructs (FIG. 3). This comparison demonstrates that higher 2-HIBA titers and, thus, higher productivities can be achieved in *C. necator* with the RCM-dependent pathway. Significant reductions in 2-HIBA levels were observed for the RCM strains during the media-starvation phase of the fermentation run, with the final titers for all four strains being below 0.3 g/L after 24 hours culturing without media supplementation.

This is consistent with the RCM-dependent pathway operating in the reverse direction to enable *C. necator* to utilize 2-HIBA as a carbon source once the preferred carbon source, fructose, has been exhausted.

The following section provides further illustration of the methods and materials of the present invention. These Examples are illustrative only and are not intended to limit the scope of the invention in any way.

EXAMPLES

A series of 2-hydroxyisobutyric acid-producing *C. necator* strains expressing either (S)-3-hydroxybutyryl-CoA mutase (HCM) from *A. tertiaricarbonis* L108 or a (R)-3-hydroxybutyryl-CoA mutase (RCM) from *Kyrpidia tusciae* or *Bacillus massiliosenegalensis* were constructed and tested.

Gene Selection and RCM/HCM Expression Vector Construction

For each (R/S)-3-hydroxyisobutyryl-CoA mutase enzyme tested, expression constructs were assembled from separate synthetic genes coding for the enzyme-specific MeaB/MeaH G-protein chaperone, and the large and small subunits to CoA mutases themselves. To maximize substrate availability, larger synthetic operons were also assembled that co-expressed the *C. necator* acetoacetyl CoA transferase, PhaA, and either the *C. necator* (R)-3-hydroxybutyryl-CoA dehydrogenase, PhaB1, or one of two (S)-3-hydroxybutyryl-CoA dehydrogenases (*C. necator* PaaH1 and *Clostridium acetobutylicum* Hbd) for the R and S-enantiospecific CoA mutases, respectively (FIG. 2). All synthetic genes were codon-optimized for expression in *C. necator*. All vectors were assembled by standard cloning techniques such as described, for example in Green and Sambrook, Molecular Cloning, A Laboratory Manual, Nov. 18, 2014.

Construction of 2-HIBA-Producing *C. necator* Strains Expressing (R/S)-3-Hydroxybutyryl-CoA Mutase Ten 2-HIBA test strains were created by transforming, by electroporation, the complete RCM/HCM expression vector series into the *C. necator* H16 ΔphaC1 knockout strain and the three *A. tertiaricarbonis* HCM constructs into the *C. necator* H16 ΔphaC1AB1 knockout strain. Transformants were selected on TSB agar plates with appropriate antibiotic.

Fed-Batch Fermentation of 2-HIBA-Producing *C. necator* Strain

Seed Train

Cultures were first incubated overnight and then subcultured and further incubated for 16 hours. These were used as a direct inoculum for the fermentation fed batch cultures.

Fermentation

The Sartorious Ambr15F platform was used to screen the 2-HIBA production strains in a fed batch mode of operation. This system allowed control of multiple variables such as dissolved oxygen and pH. Each vessel (total volume 15 ml) was loaded with 8 ml of batch growth media which included 0.1 g/L vitamin B12. Initial agitation was set at 1500 rpm, pH control at 6.6 and aeration at 0.1 ml/min. Typically, the following process conditions were standardized and run following manufacturer instructions.

Vessels were inoculated directly from seed trains (described above) to give a final starting $OD_{600}$ of 0.2 (typically a 1% vv transfer). The cultures were allowed to grow in batch mode for approximately 12 hours which would invariably coincide with a DO of 80-90%. At this point, the cultures were induced with arabinose added to a final concentration of 0.3% w/v and the fed-batch phase of the fermentation was initiated by continuously adding feed media (including 0.1 g/L vitamin $B_{12}$) at a rate of 1.5 µl/min for 36 hours. The fermentations were continued for a further 24 hours without media supplementation, to assess the effect of carbon-limitation of 2-HIBA production. To measure 2-HIBA accumulation in the fermentation media, 500 µl culture samples were periodically taken during the fermentation experiment, to approximately coincide with growth stages of induction (12 hours after inoculation), 12 hours post-induction (24 hours after inoculation), end of feed (48 hours after inoculation) and end of run (72 hours).

Sample Preparation for Analysis

Extracellular 2-HIBA from culture samples was quantitated using liquid chromatography-mass spectrometry (LC-MS). Samples volumes were 500 µl and from this, 100 µl was used for $OD_{600}$ determination and 400 µl processed for analysis. Broth samples were centrifuged and the resulting supernatants were diluted in 90% LC-MS grade acetonitrile/10% LC-MS grade water between 10- and 1000-fold, depending upon anticipated analyte concentration.

Measurement of 2-Hydroxyisobutyrate by LC-MS

LC-MS was performed using an Agilent Technologies (Santa Clara, Calif., USA) 1290 Series Infinity HPLC system, coupled to an Agilent 6530 Series Q-TOF mass spectrometer. Manufacturer instructions were followed using a BEH Amide UPLC column: 2.1 mm diameter×50 mm length×1.7 µm particle size (Waters, Milford, Mass., USA).

External standard curves were used for quantitation. Calibration levels of 0.01, 0.02, 0.05, 0.1, 0.2, 0.5, 1, 2, 5 and 10 µg/ml were constructed in a matrix-matched solution, typically the blank medium, diluted to the same level as the samples in acetonitrile. Concentrations were determined by interpolation of sample responses against the calibration curve, using Agilent MassHunter Quantitative Analysis software.

Titration Series of Different Vitamin B12 Analogues

A *C. necator* H16 ΔA0006-9 ΔphaC1 strain was constructed expressing *Bacillus massiliosenegalensis* RcmA (SEQ ID NO: 15) *Bacillus massiliosenegalensis* RcmB (SEQ ID NO: 17) and *Bacillus massiliosenegalensis* MeaB (SEQ ID NO: 13). The genes were codon optimized for expression in *C. necator*.

Precultures (10 ml TSB, 300 µg/ml kanamycin) were set up with independent plasmid transformants of this strain and incubated at 30° C., 230 rpm, until stationary phase was reached ($OD_{600}$>1.5 AU).

The cells from each preculture were pelleted by centrifugation at 3220 g for 15 minutes, resuspended in 1 ml batch growth medium, then used to inoculate 50 ml batch growth media supplemented with 300 µg/l kanamycin. Cultures were incubated at 30° C., 230 rpm to $OD_{600}$~0.6-0.7 before RCM expression was induced with 0.3% (w/v) solution of L-arabinose. Cobalamin (vitamin B12) analogues (cyanocobalamin, CN/Cbl; adenosylcobalamin, Ad-Cbl; methylcobalamin; Me-Cbl; hydroxocobalamin, OH-Cbl; dicyanocobalamin, diCN-Cbl) were added to the cultures at relevant amounts to make final concentrations of 0.1 mg/L, 0.5 mg/L, 1 mg/L, 10 mg/L and 25 mg/L of cobalamin (vitamin B12) analogs. The cultures were further incubated at 30° C., 230 rpm for 38-40 hours.

500 µl culture samples were clarified by centrifugation at ≈21,000 g for 30 minutes and used for 2-hydroxyisobutyrate LC-MS analysis as described in Example "Measurement of 2-Hydroxyisobutyrate by LC-MS".

The values in Table 1 below represent 2-HIBA concentrations in ppm (i.e., mg/L).

TABLE 1

| B12 conc. (ppm) | Vitamin B12 (i.e., cobalamin) analogue | | | | |
|---|---|---|---|---|---|
| | CN-Cbl | Ad-Cbl | Me-Cbl | OH-Cbl | diCN-Cbl |
| 0 | 0 | 0 | 0 | 0 | 0 |
| 0.1 | 188.2 | 154.1 | 224.5 | 216.8 | 0 |
| 0.5 | 257.4 | 234.8 | 258.8 | 251.9 | 0 |
| 1 | 235.7 | 206.5 | 288.1 | 262 | 0 |
| 10 | 196.8 | 231.9 | 252.9 | 262.8 | 0 |
| 25 | 217.9 | 289.3 | 309.4 | 298.3 | 15.7 |

Figure 4:
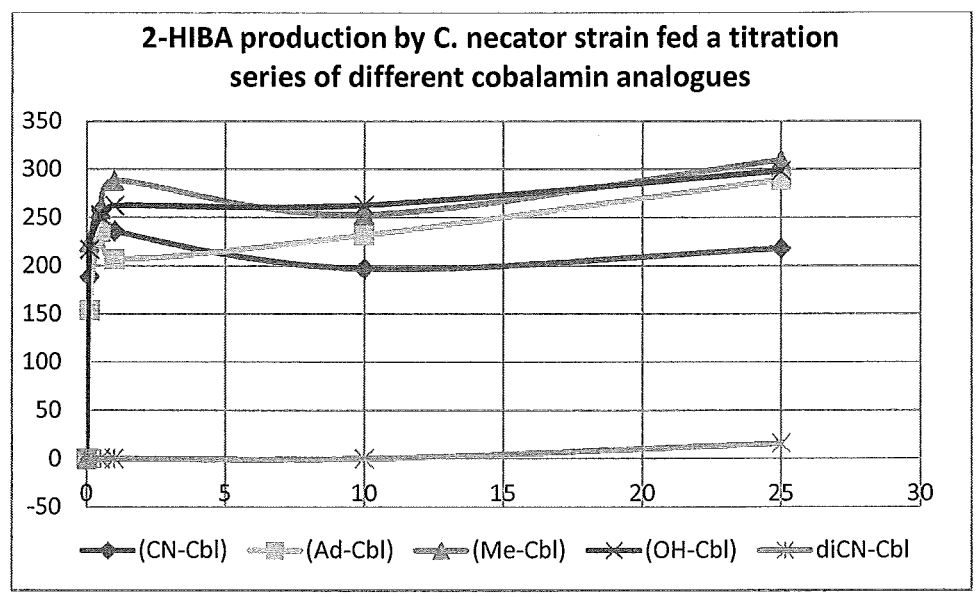
FIG. 4 is a graph showing 2-HIBA production in a *C. necator* strain fed a titration series of cobalamin analogues.
Figure 5:
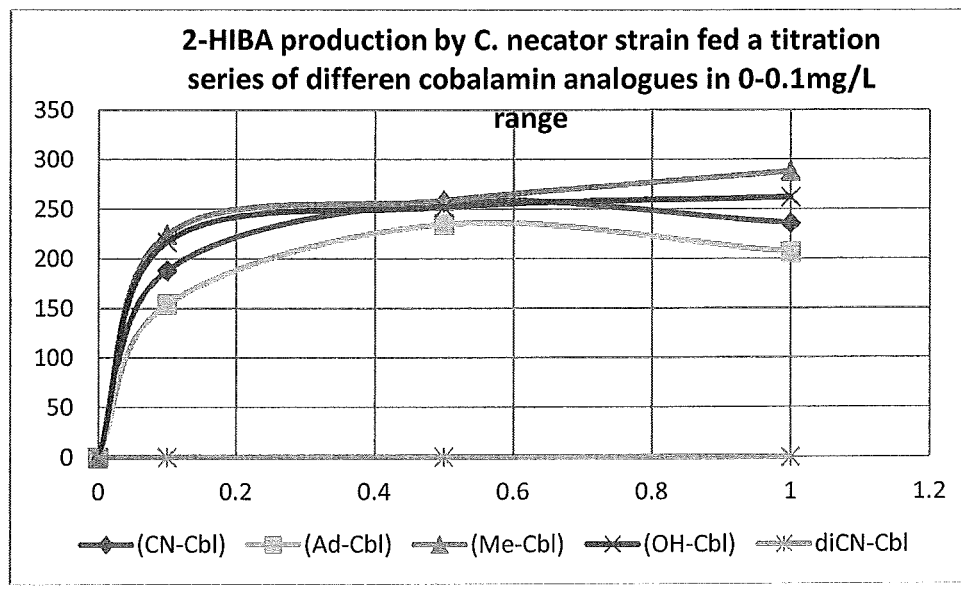
FIG. 5 is a graph showing 2-HIBA production in a *C. necator* strain fed a titration series of cobalamin analogues in a range from 0-0.1 mg/L.

The results of this titration series are depicted in FIGS. 4 and 5 and show that the strain showed a best yield of 2-HIBA/$OD_{600}$ with cobalamin (vitamin B12) concentrations around 0.1-0.5 ppm. Higher concentration of cobalamin (vitamin B12) did not improve the yield of the reaction. This indicates that a limiting concentration of vitamin B12 is reached at between 0.1 and 0.5 mg/L.

Sequence Information for Sequences in Sequence Listing

TABLE 2

| SEQ ID NO: | Sequence Description |
|---|---|
| 1 | Amino acid sequence of *A. tertiaricarbonis* MeaH (AFK77667) |
| 2 | Nucleic acid sequence of *A. tertiaricarbonis* MeaH (AFK77667) codon optimized for *C. necator* expression |
| 3 | Amino acid sequence of *A. tertiaricarbonis* large subunit HcmA (AFK77668) |
| 4 | Nucleic acid sequence of *A. tertiaricarbonis* large subunit HcmA (AFK77668) codon optimized for *C. necator* expression |
| 5 | Amino acid sequence of *A. tertiaricarbonis* large subunit HcmB (AFK77665) |
| 6 | Nucleic acid sequence of *A. tertiaricarbonis* large subunit HcmB (AFK77665) codon optimized for *C. necator* expression |
| 7 | Amino acid sequence of *K. tusciae* MeaB (WP_013074529) |
| 8 | Nucleic acid sequence of *K. tusciae* MeaB (WP_013074529) codon optimized for *C. necator* expression |
| 9 | Amino acid sequence of *K. tusciae* RcmA (WP_013074530) |
| 10 | Nucleic acid sequence of *K. tusciae* RcmA (WP_013074530) codon optimized for *C. necator* expression |
| 11 | Amino acid sequence of *K. tusciae* RcmB (WP_013074531) |
| 12 | Nucleic acid sequence of *K. tusciae* RcmB (WP_013074531) codon optimized for *C. necator* expression |
| 13 | Amino acid sequence of *B. massiliosenegalensis* MeaB (WP_019152978) |
| 14 | Nucleic acid sequence of *B. massiliosenegalensis* MeaB (WP_019152978) codon optimized for *C. necator* expression |
| 15 | Amino acid sequence of *B. massiliosenegalensis* RcmA (WP_019152977) |
| 16 | Nucleic acid sequence of *B. massiliosenegalensis* RcmA (WP_019152977) codon optimized for *C. necator* expression |
| 17 | Amino acid sequence of *B. massiliosenegalensis* RcmB (WP_019152976) |
| 18 | Nucleic acid sequence of *B. massiliosenegalensis* RcmB (WP_019152976) codon optimized for *C. necator* expression |
| 19 | Amino acid sequence of *C. necator* PhaA (WP_010810132) |
| 20 | Nucleic acid sequence of *C. necator* PhaA (WP_010810132) |
| 21 | Amino acid sequence of *C. necator* PaaH1 (WP_010814882) |
| 22 | Nucleic acid sequence of *C. necator* PaaH1 (WP_010814882) codon optimized for *C. necator* expression |
| 23 | Amino acid sequence of *Clostridium acetobutylicum* Hbd (WP_010965995) |
| 24 | Nucleic acid sequence of *Clostridium acetobutylicum* Hbd (WP_010965995) codon optimized for *C. necator* expression |
| 25 | Amino acid sequence of *C. necator* PhaB1 (WP_010810131) |
| 26 | Nucleic acid sequence of *C. necator* PhaB1 (WP_010810131) codon optimized for *C. necator* expression |

What is claimed is:

1. A process for the biosynthesis of 2-hydroxisobutyric acid (2-HIBA), and/or derivatives thereof and/or compounds related thereto, said process comprising:
   obtaining a *Cupriavidus necator* organism capable of producing 2-HIBA, derivatives thereof and/or compounds related thereto;
   engineering the *C. necator* organism to abolish polyhydroxyalkanoate (PHA) synthase activity;
   engineering the *C. necator* organism to express an R-enantioselective 3-hydroxybutyryl CoA mutase (RCM) comprising *Bacillus massiliosenegalensis* RcmA comprising the amino acid sequence of SEQ ID NO: 15 or *Bacillus massiliosenegalensis* RcmB comprising the amino acid sequence of SEQ ID NO: 17; and
   overexpressing an acetoacetyl-CoA transferase, PhaA; and
   culturing the engineered *C. necator* organism to produce 2-fold or higher levels of 2-HIBA by the engineered *C. necator* organism as compared to a *C. necator* organism engineered to express (S)-3-hydroxybutyryl-CoA mutase (HCM).

2. The process of claim 1, wherein the acetoacetyl-CoA transferase, PhaA, is a *C. necator* acetoacetyl-CoA transferase, PhaA comprising the amino acid sequence of SEQ ID NO: 19.

* * * * *

SEQUENCE LISTING

```
<160> NUMBER OF SEQ ID NOS: 26

<210> SEQ ID NO 1
<211> LENGTH: 327
<212> TYPE: PRT
<213> ORGANISM: A. tertiaricarbonis

<400> SEQUENCE: 1

Met Thr Tyr Val Pro Ser Ser Ala Leu Leu Glu Gln Leu Arg Ala Gly
1               5                   10                  15

Asn Thr Trp Ala Leu Gly Arg Leu Ile Ser Arg Ala Glu Ala Gly Val
            20                  25                  30

Ala Glu Ala Arg Pro Ala Leu Ala Glu Val Tyr Arg His Ala Gly Ser
        35                  40                  45

Ala His Val Ile Gly Leu Thr Gly Val Pro Gly Ser Gly Lys Ser Thr
    50                  55                  60

Leu Val Ala Lys Leu Thr Ala Ala Leu Arg Lys Arg Gly Glu Lys Val
65                  70                  75                  80

Gly Ile Val Ala Ile Asp Pro Ser Ser Pro Tyr Ser Gly Gly Ala Ile
                85                  90                  95

Leu Gly Asp Arg Ile Arg Met Thr Glu Leu Ala Asn Asp Ser Gly Val
            100                 105                 110

Phe Ile Arg Ser Met Ala Thr Arg Gly Ala Thr Gly Gly Met Ala Arg
        115                 120                 125

Ala Ala Leu Asp Ala Val Asp Leu Leu Asp Val Ala Gly Tyr His Thr
    130                 135                 140
```

```
Ile Ile Leu Glu Thr Val Gly Val Gly Gln Asp Glu Val Glu Val Ala
145                 150                 155                 160

His Ala Ser Asp Thr Thr Val Val Val Ser Ala Pro Gly Leu Gly Asp
                165                 170                 175

Glu Ile Gln Ala Ile Lys Ala Gly Val Leu Glu Ile Ala Asp Ile His
            180                 185                 190

Val Val Ser Lys Cys Asp Arg Asp Ala Asn Arg Thr Leu Thr Asp
        195                 200                 205

Leu Lys Gln Met Leu Thr Leu Gly Thr Met Val Gly Pro Lys Arg Ala
    210                 215                 220

Trp Ala Ile Pro Val Val Gly Val Ser Ser Tyr Thr Gly Glu Gly Val
225                 230                 235                 240

Asp Asp Leu Leu Gly Arg Ile Ala Ala His Arg Gln Ala Thr Ala Asp
                245                 250                 255

Thr Glu Leu Gly Arg Glu Arg Arg Arg Val Ala Glu Phe Arg Leu
            260                 265                 270

Gln Lys Thr Ala Glu Thr Leu Leu Leu Glu Arg Phe Thr Thr Gly Ala
        275                 280                 285

Gln Pro Phe Ser Pro Ala Leu Ala Asp Ser Leu Ser Asn Arg Ala Ser
    290                 295                 300

Asp Pro Tyr Ala Ala Arg Glu Leu Ile Ala Arg Thr Ile Arg Lys
305                 310                 315                 320

Glu Tyr Ser Asn Asp Leu Ala
                325
```

<210> SEQ ID NO 2
<211> LENGTH: 984
<212> TYPE: DNA
<213> ORGANISM: Artificial sequence
<220> FEATURE:
<223> OTHER INFORMATION: Synthetic

<400> SEQUENCE: 2

```
atgacctatg tgccctcctc ggcgctgctc gaacagctcc gcgccggtaa cacctgggcc      60
ctgggccgcc tgatctcccg cgcggaagcg ggcgtggcgg aagcccgccc cgccctggcc     120
gaggtgtacc ggcatgccgg cagcgcccac gtgatcggtc tgaccggcgt cccgggctcg     180
ggcaagtcca ccctggtcgc caagctcacc gccgccctgc gcaagcgcgg cgaaaaggtc     240
ggcatcgtcg cgatcgatcc gtcgtcgccg tacagcggcg cgcgatcct gggcgaccgc      300
attcgcatga cggaactggc caacgatagc ggcgtgttca tccgcagcat ggccacccgc     360
ggcgccacgg gcggcatggc ccgggccgcc ctggacgcgg tggacctcct ggacgtggcg     420
ggctaccaca ccatcatcct ggaaaccgtg ggcgtcggcc agacgaagt cgaagtggcc      480
catgccagcg acacgaccgt ggtcgtgtcg gcccccggcc tgggcgacga gatccaggcg     540
atcaaggccg gcgtgctgga aatcgcggat atccatgtgg tgtcgaagtg cgatcgtgac     600
gacgcgaatc gcaccctcac ggacctgaag caaatgctca ccctgggtac gatggtgggc     660
ccgaagcgcg cgtgggccat cccggtcgtg ggcgtcagct cctacaccgg cgagggcgtg     720
gacgacctcc tgggccgcat tgcggcccac cggcaggcca ccgcggacac ggaactgggc     780
cgcgagcgcc gtcgcgggt cgcggagttc gcctgcaaa agacggccga aaccctgctg      840
ctggagcgtt tcaccaccgg cgcccagccg ttttcccccg cgctggccga tagcctgagc     900
```

```
aaccgcgcgt cggaccccta cgccgccgcc cgcgagctga tcgcgcgcac catccgcaag    960
gaatatagca acgacctggc ctga                                           984
```

<210> SEQ ID NO 3
<211> LENGTH: 562
<212> TYPE: PRT
<213> ORGANISM: A. tertiaricarbonis

<400> SEQUENCE: 3

```
Met Thr Trp Leu Glu Pro Gln Ile Lys Ser Gln Leu Gln Ser Glu Arg
1               5                   10                  15

Lys Asp Trp Glu Ala Asn Glu Val Gly Ala Phe Leu Lys Lys Ala Pro
            20                  25                  30

Glu Arg Lys Glu Gln Phe His Thr Ile Gly Asp Phe Pro Val Gln Arg
        35                  40                  45

Thr Tyr Thr Ala Ala Asp Ile Ala Asp Thr Pro Leu Glu Asp Ile Gly
    50                  55                  60

Leu Pro Gly Arg Tyr Pro Phe Thr Arg Gly Pro Tyr Pro Thr Met Tyr
65                  70                  75                  80

Arg Ser Arg Thr Trp Thr Met Arg Gln Ile Ala Gly Phe Gly Thr Gly
                85                  90                  95

Glu Asp Thr Asn Lys Arg Phe Lys Tyr Leu Ile Ala Gln Gly Gln Thr
            100                 105                 110

Gly Ile Ser Thr Asp Phe Asp Met Pro Thr Leu Met Gly Tyr Asp Ser
        115                 120                 125

Asp His Pro Met Ser Asp Gly Glu Val Gly Arg Glu Gly Val Ala Ile
    130                 135                 140

Asp Thr Leu Ala Asp Met Glu Ala Leu Leu Ala Asp Ile Asp Leu Glu
145                 150                 155                 160

Lys Ile Ser Val Ser Phe Thr Ile Asn Pro Ser Ala Trp Ile Leu Leu
                165                 170                 175

Ala Met Tyr Val Ala Leu Gly Glu Lys Arg Gly Tyr Asp Leu Asn Lys
            180                 185                 190

Leu Ser Gly Thr Val Gln Ala Asp Ile Leu Lys Glu Tyr Met Ala Gln
        195                 200                 205

Lys Glu Tyr Ile Tyr Pro Ile Ala Pro Ser Val Arg Ile Val Arg Asp
    210                 215                 220

Ile Ile Thr Tyr Ser Ala Lys Asn Leu Lys Arg Tyr Asn Pro Ile Asn
225                 230                 235                 240

Ile Ser Gly Tyr His Ile Ser Glu Ala Gly Ser Ser Pro Leu Gln Glu
                245                 250                 255

Ala Ala Phe Thr Leu Ala Asn Leu Ile Thr Tyr Val Asn Glu Val Thr
            260                 265                 270

Lys Thr Gly Met His Val Asp Glu Phe Ala Pro Arg Leu Ala Phe Phe
        275                 280                 285

Phe Val Ser Gln Gly Asp Phe Phe Glu Glu Val Ala Lys Phe Arg Ala
    290                 295                 300

Leu Arg Arg Cys Tyr Ala Lys Ile Met Lys Glu Arg Phe Gly Ala Arg
305                 310                 315                 320

Asn Pro Glu Ser Met Arg Leu Arg Phe His Cys Gln Thr Ala Ala Ala
                325                 330                 335

Thr Leu Thr Lys Pro Gln Tyr Met Val Asn Val Val Arg Thr Ser Leu
            340                 345                 350
```

```
Gln Ala Leu Ser Ala Val Leu Gly Gly Ala Gln Ser Leu His Thr Asn
            355                 360                 365
Gly Tyr Asp Glu Ala Phe Ala Ile Pro Thr Glu Asp Ala Met Lys Met
370                 375                 380
Ala Leu Arg Thr Gln Gln Ile Ile Ala Glu Glu Ser Gly Val Ala Asp
385                 390                 395                 400
Val Ile Asp Pro Leu Gly Gly Ser Tyr Tyr Val Glu Ala Leu Thr Thr
                405                 410                 415
Glu Tyr Glu Lys Lys Ile Phe Glu Ile Leu Glu Val Glu Lys Arg
            420                 425                 430
Gly Gly Thr Ile Lys Leu Ile Glu Gln Gly Trp Phe Gln Lys Gln Ile
            435                 440                 445
Ala Asp Phe Ala Tyr Glu Thr Ala Leu Arg Lys Gln Ser Gly Gln Lys
            450                 455                 460
Pro Val Ile Gly Val Asn Arg Phe Val Glu Asn Glu Asp Val Lys
465                 470                 475                 480
Ile Glu Ile His Pro Tyr Asp Asn Thr Thr Ala Glu Arg Gln Ile Ser
                485                 490                 495
Arg Thr Arg Arg Val Arg Ala Glu Arg Asp Glu Ala Lys Val Gln Ala
            500                 505                 510
Met Leu Asp Gln Leu Val Ala Val Ala Lys Asp Glu Ser Gln Asn Leu
            515                 520                 525
Met Pro Leu Thr Ile Glu Leu Val Lys Ala Gly Ala Thr Met Gly Asp
            530                 535                 540
Ile Val Glu Lys Leu Lys Gly Ile Trp Gly Thr Tyr Arg Glu Thr Pro
545                 550                 555                 560
Val Phe

<210> SEQ ID NO 4
<211> LENGTH: 1689
<212> TYPE: DNA
<213> ORGANISM: Artificial sequence
<220> FEATURE:
<223> OTHER INFORMATION: Synthetic

<400> SEQUENCE: 4
atgacctggc tggagccgca aatcaagagc cagctgcaat cggagcggaa ggattgggaa    60
gcgaacgaag tgggtgcctt cctcaagaag gcccccgaac gcaaggaaca gtttcacacg   120
atcggcgact cccccgtcca gcgcacctac acggccgccg atatcgccga caccccgctg   180
gaggacatcg gcctgccggg ccgctacccg ttcacgcgcg gtccgtaccc gacgatgtat   240
cgctcccgca cctggaccat gcggcagatc gccggcttcg gcacgggcga ggacaccaac   300
aagcgtttta agtatctgat cgcccagggt caaaccggca tctcgaccga cttcgacatg   360
cccacccctga tgggctatga ttcggaccac ccgatgtccg acggcgaagt gggccgcgaa   420
ggcgtcgcga tcgacacgct cgccgacatg aagcgctgc tggccgatat cgacctggaa   480
aagatcagcg tgagcttcac catcaacccc tcagcctgga ttctgctggc gatgtacgtc   540
gccctcggcg aaaagcgcgg ctacgacctg aacaagctga gcggcaccgt gcaagccgac   600
atcctgaagg agtacatggc gcaaaaggaa tatatctacc ccatcgcccc gtcggtccgc   660
atcgtgcgtg acatcattac gtattcggcg aagaacctca gcgctataa ccccatcaac   720
attagcggct accatatctc ggaggcgggc agcagccccc tccaggaggc cgcgttcacg   780
ctcgcgaacc tgattacgta cgtgaacgag gtcaccaaga ccggcatgca tgtcgatgag   840
```

-continued

```
tttgcgccgc ggctggcgtt cttcttcgtg tcgcagggcg acttctttga agaagtcgcg    900
aagtttcgcg cgctccgccg ctgctacgcc aagatcatga aggaacgctt cggcgcccgc    960
aacccggaga gcatgcgcct ccggttccac tgccaaaccg ccgccgcgac gctgaccaag   1020
ccgcaataca tggtcaacgt ggtccgcacc tcgctgcagg cgctgtcggc cgtcctgggc   1080
ggtgcgcagt cgctccatac caatggctac gacgaagcgt tcgccatccc gacggaagat   1140
gccatgaaga tggccctgcg cacgcagcag atcattgccg aagaatccgg cgtcgccgac   1200
gtgatcgacc cgctgggcgg cagctattac gtcgaggcgc tgacgaccga atatgaaaag   1260
aagattttcg aaattctgga agaggtggag aagcgcggtg gcaccatcaa gctgatcgaa   1320
cagggctggt tccagaagca aatcgccgac ttcgcctacg aaacggcgct gcgcaagcag   1380
tcgggccaga agcccgtcat cggtgtgaac cgcttcgtgg aaaacgagga ggacgtgaag   1440
atcgagatcc acccgtacga taacaccacg gccgaacgcc agatcagccg cacccggcgg   1500
gtgcgtgccg agcgcgacga ggccaaggtc caggcgatgc tggaccagct cgtcgcggtg   1560
gcgaaggatg agagccagaa cctgatgccg ctgaccatca gctcgtgaa ggccggcgcc   1620 acgatgggcg acatcgtgga aaagctcaag ggcatctggg gcacgtaccg cgaaacgccg   1680
gtgttctga                                                         1689
```

<210> SEQ ID NO 5
<211> LENGTH: 136
<212> TYPE: PRT
<213> ORGANISM: A. tertiaricarbonis

<400> SEQUENCE: 5

```
Met Asp Gln Thr Pro Ile Arg Val Leu Leu Ala Lys Val Gly Leu Asp
1               5                   10                  15

Gly His Asp Arg Gly Val Lys Val Val Ala Arg Ala Leu Arg Asp Ala
            20                  25                  30

Gly Met Asp Val Ile Tyr Ser Gly Leu His Arg Thr Pro Glu Glu Val
        35                  40                  45

Val Asn Thr Ala Ile Gln Glu Asp Val Asp Val Leu Gly Val Ser Leu
    50                  55                  60

Leu Ser Gly Val Gln Leu Thr Val Phe Pro Lys Ile Phe Lys Leu Leu
65                  70                  75                  80

Asp Glu Arg Gly Ala Gly Asp Leu Ile Val Ile Ala Gly Gly Val Met
                85                  90                  95

Pro Asp Glu Asp Ala Ala Ala Ile Arg Lys Leu Gly Val Arg Glu Val
            100                 105                 110

Leu Leu Gln Asp Thr Pro Pro Gln Ala Ile Ile Asp Ser Ile Arg Ser
        115                 120                 125

Leu Val Ala Ala Arg Gly Ala Arg
    130                 135
```

<210> SEQ ID NO 6
<211> LENGTH: 411
<212> TYPE: DNA
<213> ORGANISM: Artificial sequence
<220> FEATURE:
<223> OTHER INFORMATION: Synthetic

<400> SEQUENCE: 6

```
atggaccaga cgccgatccg cgtcctgctg gccaaggtcg gcctggacgg ccatgatcgc     60
ggcgtcaagg tcgtcgcccg cgccctgcgc gacgccggta tggacgtgat ctactccggc    120
```

```
ctgcaccgca cgcccgaaga agtcgtcaac accgcgatcc aggaagatgt ggacgtgctg    180
ggcgtgtcgc tcctgagcgg cgtgcagctg accgtgttcc cgaagatttt caagctgctc    240
gacgagcggg gcgccggcga cctgatcgtg atcgccggtg gcgtgatgcc ggacgaagat    300
gcggcggcca tccggaagct gggcgtgcgc gaggtgctgc tgcaagacac cccccccgcag   360 gcgatcatcg actcgatccg cagcctcgtg gcggcccgtg gcgcgcgctg a             411
```

<210> SEQ ID NO 7
<211> LENGTH: 312
<212> TYPE: PRT
<213> ORGANISM: K. tusciae

<400> SEQUENCE: 7

```
Met Gln Glu Leu Leu Ser Arg Phe Asp Ala Gly Asp Pro Val Ala Leu
1               5                   10                  15

Gly Lys Leu Leu Lys Glu Val Glu Asn Gly Thr Ser Ser Gly Lys Glu
            20                  25                  30

Ala Leu Arg Cys Thr Ala Ser Arg Gln Gly Arg Ala His Val Val Gly
        35                  40                  45

Ile Thr Gly Pro Pro Gly Ala Gly Lys Ser Thr Leu Thr Ala Lys Leu
    50                  55                  60

Ser Lys Arg Trp Ala Glu Ala Gly Arg Glu Val Gly Ile Val Cys Val
65                  70                  75                  80

Asp Pro Thr Ser Pro Phe Ser Gly Gly Ala Leu Leu Gly Asp Arg Ile
                85                  90                  95

Arg Met Leu Glu Leu Ser Ser Phe Pro Asn Val Phe Ile Lys Ser Leu
            100                 105                 110

Ala Thr Arg Gly Ser Leu Gly Gly Met Ala Ala Ser Thr Ala Asp Ile
        115                 120                 125

Ile Gln Leu Met Asp Ala Tyr Gly Lys Glu Val Val Val Glu Thr
    130                 135                 140

Val Gly Val Gly Gln Val Glu Phe Asp Val Met Asp Leu Ser Asp Thr
145                 150                 155                 160

Val Val Leu Val Asn Val Pro Gly Leu Gly Asp Ser Ile Gln Ala Leu
                165                 170                 175

Lys Ala Gly Ile Leu Glu Ile Ala Asp Ile Phe Val Ile Asn Gln Ala
            180                 185                 190

Asp Arg Pro Gly Ala Glu Asp Ser Val Arg Asp Leu Arg Gln Met Leu
        195                 200                 205

Ala Asp Arg Lys Glu Thr Gly Trp Leu Trp Pro Val Val Lys Thr Val
    210                 215                 220

Ala Thr Arg Gly Glu Gly Ile Asp Arg Leu Ala Glu Ala Ile Glu Ser
225                 230                 235                 240

His Arg Ala Tyr Leu Lys Arg Glu Gln Leu Trp Glu Lys Arg Cys
                245                 250                 255

Arg Arg Asn Arg Gln Arg Leu Met Gln Glu Met Asp Arg Leu Phe Arg
            260                 265                 270

Gln His Val Leu Thr Arg Ile Arg Thr Asp Pro Thr Ala Arg Ala Leu
        275                 280                 285

Phe Glu Glu Val Glu Lys Gly Thr Gln Asp Pro Tyr Ser Ala Ala Arg
    290                 295                 300

His Leu Phe Gln Glu Ile Val Asn
305                 310
```

<210> SEQ ID NO 8
<211> LENGTH: 939
<212> TYPE: DNA
<213> ORGANISM: Artificial sequence
<220> FEATURE:
<223> OTHER INFORMATION: Synthetic

<400> SEQUENCE: 8

```
atgcaggaac tgctgtcgcg cttcgacgcg ggcgaccccg tcgccctggg caagctgctg      60
aaggaagtgg agaacggcac gtccagcggc aaggaagcgc tgcgctgcac ggccagccgt     120
cagggccggg cgcacgtcgt cggcatcacc ggccccccgg gtgcgggcaa gtccacgctg     180
acggccaagc tgtcgaagcg ctgggccgaa gcgggccgcg aggtcggcat cgtctgcgtc     240
gatccgacga gccccttctc cggcggcgcg ctgctgggtg accggattcg catgctggag     300
ctgagctcct cccgaatgt gttcatcaag tcgctcgcca cccgcggctc gctgggcggt     360
atggccgcct cgacggcgga catcatccag ctgatggacg cgtacggtaa ggaagtcgtg     420
gtggtggaaa ccgtgggtgt gggccaagtg gagtttgacg tgatggacct gtcggatacg     480
gtcgtgctcg tcaacgtgcc gggcctcggc gattcgatcc aggcgctgaa ggccggcatc     540
ctggagattg ccgatatctt cgtgatcaac caggccgacc gccgggcgc cgaggactcg     600
gtgcgggatc tgcgccagat gctggcggat cgcaaggaaa ccggctggct gtggccggtc     660
gtcaagaccg tggcgacgcg cggcgaaggc atcgatcgtc tggccgaagc gatcgagtcc     720
atcgcgcct acctgaagcg cgagcagctg tgggaagaga agcgctgccg gcgcaaccgg     780
caacgcctga tgcaggaaat ggaccgcctg ttccgccaac acgtgctcac ccgcatccgc     840
acggacccca ccgcccgtgc cctgttcgaa gaagtggaaa agggcaccca ggacccgtat     900
agcgccgccc gccatctctt ccaggaaatc gtgaattga                            939
```

<210> SEQ ID NO 9
<211> LENGTH: 563
<212> TYPE: PRT
<213> ORGANISM: K. tusciae

<400> SEQUENCE: 9

```
Met Ala Asp Gln Glu Lys Leu Phe Asn Gly Asp Glu Ile Arg Arg Ile
1               5                   10                  15

Arg Gln Glu Lys Glu Arg Trp Tyr Arg Glu Thr Val Lys Gly Asn Asp
            20                  25                  30

Gly Gly Asn Asp Tyr Val Thr Asp Ser Gly Ile Pro Val Asn Leu Ile
        35                  40                  45

Tyr Gly Pro Asp Asp Ile Ala Asp Phe Asp Tyr Leu Lys Glu Ser Gly
    50                  55                  60

Phe Ser Gly Glu Pro Pro Tyr Val Arg Gly Val Tyr Pro Asn Met Tyr
65                  70                  75                  80

Arg Gly Arg Leu Phe Thr Ile Arg Gln Ile Ala Gly Phe Gly Thr Pro
                85                  90                  95

Glu Asp Thr Asn Arg Arg Phe Lys Phe Leu Leu Glu Asn Gly Ala Thr
            100                 105                 110

Gly Thr Ser Val Val Leu Asp Leu Pro Thr Ile Arg Gly Tyr Asp Ser
        115                 120                 125

Asp Asp Pro Lys Ala Glu Gly His Val Gly Ala Ala Gly Val Ala Ile
    130                 135                 140

Asp Ser Leu Glu Asp Met Glu Ala Leu Tyr Asp Gly Ile Pro Ile Asp
145                 150                 155                 160
```

```
Gln Val Ser Ser Asn Ile Val Thr His Leu Pro Ser Thr Thr Val Val
                165                 170                 175
Leu Met Ala Met Phe Val Ala Met Ala Glu Lys Arg Gly Leu Pro Leu
            180                 185                 190
Glu Lys Leu Ser Gly Thr Asn Gln Asn Asp Phe Leu Met Glu Thr Thr
        195                 200                 205
Ile Gly Ser Ser Leu Glu Ile Leu Pro Pro Lys Ala Ser Phe Arg Leu
    210                 215                 220
Gln Cys Asp Ser Ile Glu Tyr Ala Ser Lys Arg Leu Pro Arg Trp Asn
225                 230                 235                 240
Pro Val Ser Tyr Asn Gly Tyr Asn Leu Arg Glu Ala Gly Thr Thr Ala
                245                 250                 255
Val Gln Glu Val Gly Cys Ala Ile Ala Asn Ala Ile Ala Thr Thr Glu
            260                 265                 270
Glu Leu Ile Arg Arg Gly Asn Asp Val Asp Asp Phe Ala Lys Arg Leu
        275                 280                 285
Ser Phe Phe Trp Asn Leu Phe Asn Asp Phe Phe Glu Glu Ile Ala Lys
    290                 295                 300
Cys Arg Ala Ser Arg Leu Val Trp Tyr Asp Val Met Lys Asn Arg Phe
305                 310                 315                 320
Gly Ala Lys Asn Pro Arg Ser Tyr Leu Met Arg Phe His Val Gln Thr
                325                 330                 335
Gly Gly Ile Thr Leu Thr Lys Val Glu Pro Leu Asn Asn Ile Ala Arg
            340                 345                 350
Ser Ala Ile Gln Gly Leu Ala Ala Val Leu Gly Gly Ala Gln Ser Leu
        355                 360                 365
His Ile Asp Ser Tyr Asp Glu Ala Tyr Ser Ala Pro Thr Glu Gln Ala
    370                 375                 380
Ala Leu Val Ser Leu Arg Thr Gln Gln Ile Ile Gln Val Glu Thr Gly
385                 390                 395                 400
Val Val Asn Thr Val Asp Pro Leu Ala Gly Ser Tyr Tyr Val Glu Tyr
                405                 410                 415
Leu Thr Arg Glu Met Ala Glu His Ile Arg Ala Tyr Ile Asp Gln Ile
            420                 425                 430
Glu Ser Arg Gly Gly Ile Ile Ala Val Val Glu Ser Gly Trp Leu His
        435                 440                 445
Arg Glu Ile Ala Glu Phe Ala Tyr Arg Thr Gln Gln Asp Ile Glu Thr
    450                 455                 460
Gly Lys Arg Lys Val Val Gly Leu Asn Tyr Phe Pro Ser Lys Glu Ala
465                 470                 475                 480
Glu Thr Lys Val Glu Val Phe Arg Tyr Pro Glu Asp Ala Glu Arg Met
                485                 490                 495
Gln Lys Glu Lys Leu Ala Lys Leu Arg Ala Arg Arg Asp Pro Val Lys
            500                 505                 510
Val Glu Gln Thr Leu Arg Val Leu Arg Glu Lys Cys His Glu Asp Val
        515                 520                 525
Asn Ile Leu Pro Tyr Val Lys Asp Ala Val Glu Ala Tyr Cys Thr Leu
    530                 535                 540
Gly Glu Ile Gln Asn Val Phe Arg Glu Glu Phe Gly Leu Trp Gln Phe
545                 550                 555                 560
Pro Leu Val

<210> SEQ ID NO 10
```

<211> LENGTH: 1692
<212> TYPE: DNA
<213> ORGANISM: Artificial sequence
<220> FEATURE:
<223> OTHER INFORMATION: Synthetic

<400> SEQUENCE: 10

```
atggcggacc aagaaaagct gttcaatggc gacgagattc ggcgcatccg gcaggaaaag      60
gaacggtggt atcgcgaaac cgtcaagggc aatgacggtg caatgactac cgtgaccgac     120
tcgggtattc cggtcaacct catctacggc ccggacgata tcgccgattt tgactatctg     180
aaggaaagcg gcttctccgg tgaaccgccg tacgtgcgcg cgtctaccc caatatgtac      240
cgcggccgtc tgttcaccat ccggcagatc gccggcttcg gcacgcccga ggacacgaat     300
cggcgcttca gtttctcct ggagaacggc gcgaccggca ccagcgtggt gctcgacctc      360
ccgaccatcc ggggctatga ctcggacgat ccgaaggccg agggccacgt gggcgccgcc     420
ggcgtggcga tcgactcgct ggaggacatg gaggccctgt acgatggcat cccgatcgac     480
caggtgtcct ccaacatcgt cacgcacctc ccctcgacca cggtggtcct gatggccatg     540
ttcgtcgcaa tggcggaaaa gcgtggcctg ccgctcgaaa agctgagcgg caccaaccag     600
aacgactttc tcatggaaac caccatcggc agctccctgg agattctgcc ccgaaggcc     660
tccttccgcc tccaatgcga tagcatcgag tatgcctcga agcgcctgcc ccgctggaac     720
cccgtgagct acaacggcta taatctgcgc gaggcgggca ccacggccgt ccaagaagtc     780
ggctgcgcca tcgcgaatgc catcgccacg acggaggaac tgatccgccg cggtaacgat     840
gtggacgatt tcgccaagcg cctctccttc ttctggaatc tgtttaatga cttcttcgag     900
gaaatcgcca agtgccgggc gagccgcctg gtgtggtacg acgtgatgaa gaatcgcttc     960
ggcgccaaga acccgcgctc gtacctgatg cgctttcatg tccagacggg tggcatcacc    1020
ctgaccaagg tggagccgct caacaacatt gcgcggtcgg ccattcaggg cctggccgcg    1080
gtcctgggtg cgcccagag cctgcatatc gattcgtatg atgaagcgta cagcgcgccg    1140
acggagcaag cggccctggt gtccctccgt acccagcaga tcattcaagt cgaaaccggc    1200
gtcgtgaaca cggtggaccc cctggccggc agctattacg tggagtacct gacccgcgaa    1260
atggccgagc atatccgtgc ctacatcgac caaattgaat cgcgcggtgg catcatcgcc    1320
gtggtggaga cggttggct gcaccgcgaa atcgccgagt ttgcctatcg cacgcaacaa    1380
gacattgaaa ccggcaagcg caaggtggtg ggcctgaact acttcccgag caaggaggcc    1440
gaaaccaagg tcgaagtgtt ccgttacccg gaagatgcgg aacgcatgca aaaggaaaag    1500
ctggccaagc tgcgtgcgcg ccgcgacccg gtgaaggtcg aacagaccct ccgcgtgctg    1560
cgtgagaagt gccacgaaga tgtcaacatc ctcccctatg tgaaggacgc cgtcgaggcc    1620
tactgcaccc tgggcgagat ccaaaacgtg ttccgcgagg agttcggcct gtggcagttc    1680
cccctcgtct ga                                                         1692
```

<210> SEQ ID NO 11
<211> LENGTH: 132
<212> TYPE: PRT
<213> ORGANISM: K. tusciae

<400> SEQUENCE: 11

```
Met Glu Lys Lys Ile Lys Val Ile Met Val Lys Leu Gly Leu Asp Ile
1               5                   10                  15
His Trp Arg Gly Ala Leu Val Val Ser Lys Met Leu Arg Asp Arg Gly
            20                  25                  30
```

Met Glu Val Val Tyr Leu Gly Asn Leu Phe Pro Glu Gln Ile Val Gln
                35                  40                  45

Ala Ala Val Gln Glu Gly Ala Asp Val Val Gly Leu Ser Thr Leu Gly
    50                  55                  60

Gly Asn His Leu Thr Leu Gly Pro Lys Val Val Glu Leu Leu Arg Ala
65                  70                  75                  80

Lys Gly Met Glu Glu Val Leu Val Ile Met Gly Gly Val Ile Pro Glu
                85                  90                  95

Glu Asp Val Pro Ala Leu Lys Glu Ala Gly Ile Ala Glu Val Phe Gly
                100                 105                 110

Pro Glu Thr Pro Ile Asp Ala Ile Glu Ser Phe Ile Arg Ser Arg Phe
            115                 120                 125

Pro Asp Arg Asp
            130

<210> SEQ ID NO 12
<211> LENGTH: 399
<212> TYPE: DNA
<213> ORGANISM: Artificial sequence
<220> FEATURE:
<223> OTHER INFORMATION: Synthetic

<400> SEQUENCE: 12
atggagaaga agattaaggt catcatggtg aagctgggcc tggatatcca ttggcgcggt     60
gccctggtgg tgtcgaagat gctgcgtgac cgcggcatgg aagtggtcta cctgggcaac    120
ctgtttccgg agcagatcgt ccaagccgcg gtgcaggaag gcgcggacgt ggtcggcctg    180
tccacgctgg gcggcaacca cctcaccctg ggccccaagg tcgtggagct cctgcgcgcc    240
aagggcatgg aagaagtcct ggtgatcatg ggcggcgtga tcccggaaga agatgtgccg    300
gccctcaagg aagccggcat cgcggaagtg ttcggtcccg aaaccccgat cgacgcgatc    360
gagtcgttca tccgcagccg cttcccggac cgggactga                           399

<210> SEQ ID NO 13
<211> LENGTH: 317
<212> TYPE: PRT
<213> ORGANISM: B. massiliosenegalensis

<400> SEQUENCE: 13

Met Lys Gln Ala Ala Ser Tyr Phe Glu Lys Lys Ser Asp Val Met Leu
1               5                   10                  15

Gly Lys Leu Leu Lys Glu Val Glu Asn Gln Thr Pro Thr Ser Ile Glu
                20                  25                  30

Ile Leu Lys Glu Ser Ser Ser Arg Lys Gly Asn Ala His Ile Val Gly
                35                  40                  45

Ile Thr Gly Pro Pro Gly Ser Gly Lys Ser Thr Leu Val Asn Lys Leu
        50                  55                  60

Cys Lys Thr Leu Ala Thr Ser Gly Leu Glu Ile Gly Ile Val Ala Val
65                  70                  75                  80

Asp Pro Thr Ser Pro Phe Thr Lys Gly Ala Leu Leu Gly Asp Arg Thr
                85                  90                  95

Arg Met Gln Glu Leu Ser Gly Leu Ser Asn Val Phe Ile Lys Ser Leu
                100                 105                 110

Ala Thr Arg Gly Asn Leu Gly Gly Leu Ala Pro Thr Thr Ala Asp Ile
            115                 120                 125

Val His Val Leu Asp Ala Tyr Gly Lys Glu Leu Ile Ile Ile Glu Thr
    130                 135                 140

Val Gly Val Gly Gln Ile Glu Phe Asp Val Leu Glu Ile Ala Asp Thr
145                 150                 155                 160

Val Val Leu Val Asn Val Pro Gly Leu Gly Asp Ser Leu Gln Thr Leu
                165                 170                 175

Lys Ala Gly Ile Met Glu Ile Ala Asp Ile Tyr Val Val Asn Gln Ala
            180                 185                 190

Asp Arg Pro Gly Ala Asp Glu Ser Ala Arg Asp Leu Lys Leu Met Val
        195                 200                 205

Arg Glu Lys Met Gln Asp Asn Trp Glu Gln Pro Ile Leu Lys Thr Val
    210                 215                 220

Ala Thr Asn Asn Glu Gly Ile Thr Glu Leu Ile Glu Gln Ile Gln Lys
225                 230                 235                 240

His Lys Asp Tyr Ile Lys Ser Ser Asn Ile Trp Asn Glu Lys Arg Lys
                245                 250                 255

Asn Gln Asn Leu Thr Lys Phe Asn His Leu Ile Ile Gln Thr Leu Glu
            260                 265                 270

Arg Glu Val Glu Lys Tyr Ile Ser Gly Lys Gln Asp Leu Gln Ile Lys
        275                 280                 285

Arg Gln Gln Val Lys Asp Gly Lys Leu Asp Pro Tyr Thr Leu Ser Ala
    290                 295                 300

Tyr Ile Val Gly Gln Leu Ile Glu Lys His Gly Gly Met
305                 310                 315

<210> SEQ ID NO 14
<211> LENGTH: 954
<212> TYPE: DNA
<213> ORGANISM: Artificial sequence
<220> FEATURE:
<223> OTHER INFORMATION: Synthetic

<400> SEQUENCE: 14
atgaagcaag cggccagcta ttttgagaag aagtccgacg tgatgctggg caagctgctg         60
aaggaagtgg agaaccagac ccccaccctcg attgagatcc tcaaggaaag ctcgtcgcgc        120
aagggcaacg cccacatcgt gggcatcacg ggcccgccgg gcagcggcaa gtccaccctg        180
gtgaataagc tgtgcaagac cctggccacg tcgggcctgg aaatcggcat cgtcgcggtg        240
gaccccacgt cgccgttcac caagggcgcg ctgctgggcg accgcacccg catgcaggaa        300
ctgagcggcc tctccaacgt gttcatcaag tcgctggcga cgcggggcaa cctgggcggt        360
ctggcgccca cgaccgccga catcgtgcat gtcctggatg cctacggcaa ggaactgatc        420
atcatcgaaa cggtgggcgt cggccagatc gagttcgacg tgctggagat tgccgacacc        480
gtcgtgctgg tcaatgtgcc gggtctgggc gactcgctgc agaccctgaa ggccggcatc        540
atggaaatcg cggacatcta cgtggtcaac caggccgatc gtccgggcgc cgacgagtcc        600
gcgcgcgacc tcaagctgat ggtccgcgag aagatgcagg ataactggga gcagccgatc        660
ctcaagaccg tggccaccaa caacgaaggc attaccgaac tgatcgagca gatccagaag        720
cacaaggact acatcaagtc gagcaacatc tggaacgaga gcgcaagaa ccagaacctg         780 accaagttca atcacctgat catccagacg ctggagcggg aagtcgagaa gtatatcagc        840
ggtaagcaag acctccagat caagcgccag caagtgaagg atggcaagct cgacccgtac        900
accctgagcg cctacatcgt cggccagctg atcgagaagc acggcggcat gtga             954

```
<210> SEQ ID NO 15
<211> LENGTH: 569
<212> TYPE: PRT
<213> ORGANISM: B. massiliosenegalensis

<400> SEQUENCE: 15
```

| | | | | | | | | | | | | | | | |
|---|---|---|---|---|---|---|---|---|---|---|---|---|---|---|---|
| Met | Thr | Lys | Ala | Asn | Val | Asn | Gln | Glu | Thr | Lys | Leu | Phe | Asn | Gln | Glu |
| 1 | | | | 5 | | | | | 10 | | | | | 15 | |
| Val | Val | Lys | Glu | Ile | Glu | Ala | Gln | Lys | Glu | Arg | Trp | Lys | Lys | Glu | Thr |
| | | | 20 | | | | | 25 | | | | | 30 | | |
| Val | Lys | Gly | Lys | Thr | Gly | Asp | Gly | Tyr | Phe | Ser | Asp | Ser | Gly | Ile | |
| | | 35 | | | | | 40 | | | | | 45 | | | |
| Pro | Val | Asn | Leu | Leu | Tyr | Thr | Pro | Asp | Asp | Met | Lys | Asp | Ile | Asp | Tyr |
| | 50 | | | | | 55 | | | | | 60 | | | | |
| Met | Lys | Asp | Ile | Gly | Leu | Ser | Gly | Glu | Ala | Pro | Tyr | Val | Arg | Gly | Val |
| 65 | | | | | 70 | | | | | 75 | | | | | 80 |
| Tyr | Pro | Asn | Met | Tyr | Arg | Gly | Arg | Leu | Phe | Thr | Val | Arg | Gln | Ile | Ala |
| | | | | 85 | | | | | 90 | | | | | 95 | |
| Gly | Tyr | Gly | Thr | Pro | Glu | Asp | Thr | Asn | Asp | Arg | Phe | Lys | Phe | Leu | Leu |
| | | | 100 | | | | | 105 | | | | | 110 | | |
| Lys | Asn | Gly | Ala | Thr | Gly | Thr | Ser | Val | Val | Leu | Asp | Leu | Pro | Thr | Ile |
| | | 115 | | | | | 120 | | | | | 125 | | | |
| Arg | Gly | Tyr | Asp | Ser | Asp | Asp | Pro | Glu | Ala | Glu | Gly | His | Val | Gly | Ala |
| | 130 | | | | | 135 | | | | | 140 | | | | |
| Ala | Gly | Val | Ala | Ile | Asp | Ser | Leu | Glu | Asp | Ile | Glu | Ala | Leu | Tyr | Asp |
| 145 | | | | | 150 | | | | | 155 | | | | | 160 |
| Gly | Ile | Pro | Ile | Asp | Glu | Ile | Ser | Ser | Asn | Ile | Val | Thr | His | Leu | Pro |
| | | | | 165 | | | | | 170 | | | | | 175 | |
| Ser | Thr | Thr | Val | Val | Ile | Met | Ala | Met | Phe | Ala | Ala | Met | Ala | Glu | Lys |
| | | | 180 | | | | | 185 | | | | | 190 | | |
| Lys | Gly | Ile | Pro | Phe | Glu | Lys | Leu | Ser | Gly | Thr | Asn | Gln | Asn | Asp | Phe |
| | | 195 | | | | | 200 | | | | | 205 | | | |
| Leu | Met | Glu | Thr | Ala | Ile | Gly | Ser | Ser | Leu | Glu | Val | Leu | Pro | Pro | Lys |
| | 210 | | | | | 215 | | | | | 220 | | | | |
| Ala | Ser | Phe | Arg | Leu | Gln | Cys | Asp | Ala | Ile | Glu | Phe | Ala | Ser | Lys | Asn |
| 225 | | | | | 230 | | | | | 235 | | | | | 240 |
| Leu | Pro | Arg | Trp | Asn | Pro | Val | Ser | Tyr | Asn | Gly | Tyr | Asn | Leu | Arg | Glu |
| | | | | 245 | | | | | 250 | | | | | 255 | |
| Ala | Gly | Thr | Asp | Ala | Val | Ala | Glu | Val | Ala | Cys | Ala | Leu | Ala | Asn | Ala |
| | | | 260 | | | | | 265 | | | | | 270 | | |
| Ile | Ala | Thr | Ser | Glu | Glu | Leu | Ile | Arg | Arg | Gly | Asn | Lys | Ile | Asp | Asp |
| | | 275 | | | | | 280 | | | | | 285 | | | |
| Phe | Ala | Lys | Arg | Leu | Ser | Phe | Phe | Trp | Asn | Leu | Tyr | Asn | Asp | Phe | Phe |
| | 290 | | | | | 295 | | | | | 300 | | | | |
| Glu | Glu | Ile | Ala | Lys | Cys | Arg | Ala | Ser | Arg | Val | Val | Tyr | Gln | Glu | Ile |
| 305 | | | | | 310 | | | | | 315 | | | | | 320 |
| Met | Lys | Glu | Arg | Phe | His | Ala | Glu | Glu | Met | Lys | Ser | Gln | Leu | Met | Arg |
| | | | | 325 | | | | | 330 | | | | | 335 | |
| Phe | His | Val | Gln | Thr | Ala | Gly | Ile | Thr | Leu | Thr | Lys | Val | Glu | Pro | Leu |
| | | | 340 | | | | | 345 | | | | | 350 | | |
| Asn | Asn | Ile | Ala | Arg | Ser | Ala | Ile | Gln | Gly | Leu | Ala | Ala | Val | Leu | Gly |
| | | 355 | | | | | 360 | | | | | 365 | | | |
| Gly | Ala | Gln | Ser | Leu | His | Val | Asp | Ser | Tyr | Asp | Glu | Ala | Tyr | Ser | Ala |
| | 370 | | | | | 375 | | | | | 380 | | | | |

Pro Thr Glu Glu Ser Ala Leu Ile Ser Ile Arg Thr Gln Gln Ile Ile
385                 390                 395                 400

Gln Thr Glu Thr Asn Val Val Asn Thr Val Asp Pro Leu Ala Gly Ser
            405                 410                 415

Tyr Phe Val Glu Tyr Leu Thr Lys Glu Met Ala Gln Arg Ile Arg Asp
        420                 425                 430

Tyr Ile Ser Glu Ile Glu Ser Arg Gly Gly Leu Val Ala Cys Val Asp
        435                 440                 445

Ser Gly Trp Leu His Arg Glu Ile Ala Asp Phe Ala Tyr Gln Thr Gln
    450                 455                 460

Lys Glu Ile Glu Asn Gly Thr Arg Lys Ile Val Gly Leu Asn Tyr Phe
465                 470                 475                 480

Pro Ser Glu Asp His Ala Gly Gln Lys Val Glu Val Phe Arg Tyr Pro
            485                 490                 495

Glu Thr Ala Glu Ala Lys Gln Lys Glu Lys Leu Glu Arg Leu Arg Gln
        500                 505                 510

Lys Arg Asp Ala Lys Lys Val Glu Lys Leu Asn Val Ile Arg Glu
        515                 520                 525

Met Cys His Gln Asp Val Asn Leu Met Pro Tyr Ile Lys Asp Ala Val
    530                 535                 540

Leu Glu Tyr Ala Thr Leu Gly Glu Ile Glu Glu Val Phe Arg Glu Glu
545                 550                 555                 560

Phe Gly Leu Trp Gln Phe Pro Leu Ala
            565

<210> SEQ ID NO 16
<211> LENGTH: 1710
<212> TYPE: DNA
<213> ORGANISM: Artificial sequence
<220> FEATURE:
<223> OTHER INFORMATION: Synthetic

<400> SEQUENCE: 16
atgacgaagg cgaatgtgaa ccaggaaacc aagctgttca accaagaagt ggtgaaggaa      60
atcgaggccc aaaaggaacg ctggaagaag gaaaccgtca agggcaagac cggcgacggc     120
gagtacttca gcgactcggg catcccggtg aacctcctgt acacgcccga cgatatgaaa     180
gacatcgact acatgaagga catcggcctg tcgggcgagg cgccctatgt gcgtggcgtc     240
tacccgaata tgtaccgcgg ccgtctgttc accgtgcgcc agatcgccgg ttacggcacc     300
cccgaggaca ccaacgaccg ctttaagttc ctgctgaaga acggcgccac gggcacgtcg     360
gtcgtcctcg atctgcccac gatccgtggc tacgattcgg acgacccgga agccgagggc     420
catgtgggtg ccgcgggcgt cgcgatcgac tcgctggaag atatcgaggc gctgtacgac     480
ggtatcccga tcgacgagat cagcagcaac atcgtgaccc atctcccgtc caccaccgtc     540
gtgatcatgg cgatgttcgc ggcgatggcc gagaagaagg gcatcccgtt cgagaagctg     600
agcggcacca accagaacga cttcctgatg gaaaccgcca tcggctccag cctggaagtc     660
ctgccgccga aggccagctt ccggctgcag tgcgacgcga tcgagtttgc ctcgaagaac     720
ctcccgcgct ggaaccccgt gtcgtataac ggctacaatc tgcgcgaggc cggtacggac     780
gcggtggccg aagtggcctg cgcgctggcc aatgccatcg cgacctcgga agaactgatc     840
cgccgcggca acaagatcga tgacttcgcc aagcgcctgt cgttcttctg gaacctgtat     900
aacgatttct tcgaagagat gcgaagtgc cgcgcctcgc gcgtggtgta ccaggaaatc     960

```
atgaaggaac gcttccacgc cgaagagatg aagtcgcagc tcatgcgctt ccacgtgcag    1020
accgccggca tcaccctgac caaggtcgag ccgctgaaca acattgcgcg cagcgccatt    1080
cagggcctgg cggccgtcct cggcggtgcc cagagcctgc atgtggactc ctacgacgaa    1140
gcctactccg ccccgaccga ggaatccgcc ctgatttcga tccgcaccca gcagatcatc    1200
cagacggaaa ccaacgtcgt caacacggtg gacccgctgg cgggcagcta tttcgtggag    1260
tacctgacga aggaaatggc ccagcgcatc cgggactata tcagcgagat cgaatcgcgc    1320
ggcggcctgg tggcctgcgt ggactccggc tggctgcacc gggagatcgc ggatttcgcc    1380
taccaaaccc aaaaggaaat cgagaacggc acccgcaaga tcgtgggcct gaactacttc    1440
ccgagcgagg accacgcggg ccaaaaggtc gaggtgttcc ggtacccgga aacggcggaa    1500
gccaagcaga aggaaaagct ggagcgcctg cgccagaagc gggacgccaa gaaggtcgag    1560
gaaaagctga acgtcatccg cgagatgtgc caccaagacg tgaacctcat gccctatatc    1620
aaggacgccg tgctggaata cgcgacgctg gcgagatcg aagaagtgtt ccgcgaagag    1680
ttcggcctgt ggcagtttcc gctggcgtga                                     1710

<210> SEQ ID NO 17
<211> LENGTH: 130
<212> TYPE: PRT
<213> ORGANISM: B. massiliosenegalensis

<400> SEQUENCE: 17

Met Gln Val Lys Val Val Met Ala Lys Leu Gly Leu Asp Ile His Trp
1               5                   10                  15

Arg Gly Ala Leu Val Val Ser Arg Met Leu Arg Asp Glu Gly Met Glu
            20                  25                  30

Val Val Tyr Leu Gly Asn Gln Phe Pro Glu Gln Ile Val Glu Ala Ala
        35                  40                  45

Ile Gln Glu Gly Ala Asp Val Ile Gly Leu Ser Thr Leu Gly Gly Asn
    50                  55                  60

His Leu Thr Leu Gly Pro Lys Val Val Lys Ile Ala Arg Glu Lys Gly
65                  70                  75                  80

Val Glu Ser Leu Val Ile Met Gly Gly Val Ile Pro Glu Asp Asp Ile
                85                  90                  95

Pro Leu Leu Lys Glu Ser Gly Ile Ala Glu Val Phe Gly Pro Glu Thr
            100                 105                 110

Lys Val Glu Ser Ile Ala Ser Phe Ile Arg Glu His Val Gly Lys Lys
        115                 120                 125

Ile Gly
    130

<210> SEQ ID NO 18
<211> LENGTH: 393
<212> TYPE: DNA
<213> ORGANISM: Artificial sequence
<220> FEATURE:
<223> OTHER INFORMATION: Synthetic

<400> SEQUENCE: 18
atgcaagtga aggtcgtgat ggccaagctg ggcctggaca tccattggcg cggtgcgctc      60
gtggtgagcc gtatgctgcg cgacgaaggc atggaagtgg tgtacctggg caaccagttc     120
ccggagcaga tcgtcgaggc cgcgatccag gaaggcgcgg acgtgatcgg cctgtccacg     180
ctgggcggca accacctgac cctgggcccc aaggtcgtca gattgcccg cgaaaagggc     240
```

-continued

```
gtggagtcgc tggtcatcat gggcggtgtg atccccgaag atgacatccc gctgctcaag    300
gaatcgggca tcgccgaggt gttcggcccg gaaaccaagg tcgagagcat cgcctcgttc    360
atccgggagc acgtgggcaa gaagatcggc tga                                 393
```

<210> SEQ ID NO 19
<211> LENGTH: 393
<212> TYPE: PRT
<213> ORGANISM: C. necator

<400> SEQUENCE: 19

```
Met Thr Asp Val Val Ile Val Ser Ala Ala Arg Thr Ala Val Gly Lys
1               5                   10                  15

Phe Gly Gly Ser Leu Ala Lys Ile Pro Ala Pro Glu Leu Gly Ala Val
            20                  25                  30

Val Ile Lys Ala Ala Leu Glu Arg Ala Gly Val Lys Pro Glu Gln Val
        35                  40                  45

Ser Glu Val Ile Met Gly Gln Val Leu Thr Ala Gly Ser Gly Gln Asn
    50                  55                  60

Pro Ala Arg Gln Ala Ala Ile Lys Ala Gly Leu Pro Ala Met Val Pro
65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
            100                 105                 110

Gly Gly Gln Glu Asn Met Ser Ala Ala Pro His Val Leu Pro Gly Ser
        115                 120                 125

Arg Asp Gly Phe Arg Met Gly Asp Ala Lys Leu Val Asp Thr Met Ile
    130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
        195                 200                 205

Gly Asp Pro Val Ala Phe Lys Thr Asp Glu Phe Val Arg Gln Gly Ala
    210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
        275                 280                 285

Met Gly Met Gly Pro Val Pro Ala Ser Lys Arg Ala Leu Ser Arg Ala
    290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350
```

Ala Ser Gly Cys Arg Ile Leu Val Thr Leu Leu His Glu Met Lys Arg
         355                 360                 365

Arg Asp Ala Lys Lys Gly Leu Ala Ser Leu Cys Ile Gly Gly Gly Met
     370                 375                 380

Gly Val Ala Leu Ala Val Glu Arg Lys
385                 390

<210> SEQ ID NO 20
<211> LENGTH: 1182
<212> TYPE: DNA
<213> ORGANISM: C. necator

<400> SEQUENCE: 20

```
atgactgacg ttgtcatcgt atccgccgcc cgcaccgcgg tcggcaagtt tggcggctcg      60
ctggccaaga tcccggcacc ggaactgggt gccgtggtca tcaaggccgc gctggagcgc     120
gccggcgtca agccggagca ggtgagcgaa gtcatcatgg ccaggtgctg accgccggt      180
tcgggccaga accccgcacg ccaggccgcg atcaaggccg gctgccggc gatggtgccg      240
gccatgacca tcaacaaggt gtgcggctcg ggcctgaagg ccgtgatgct ggccgccaac     300
gcgatcatgg cgggcgacgc cgagatcgtg gtggccggcg gccaggaaaa catgagcgcc     360
gccccgcacg tgctgccggg ctcgcgcgat ggtttccgca tgggcgatgc caagctggtc     420
gacaccatga tcgtcgacgg cctgtgggac gtgtacaacc agtaccacat ggcatcacc     480
gccgagaacg tggccaagga atacggcatc acacgcgagg cgcaggatga gttcgccgtc     540
ggctcgcaga acaaggccga agccgcgcag aaggccggca gtttgacga agagatcgtc     600
ccggtgctga tcccgcagcg caagggcgac ccggtggcct tcaagaccga cgagttcgtg     660
cgccagggcg ccacgctgga cagcatgtcc ggcctcaagc ccgccttcga caaggccggc     720
acggtgaccg cggccaacgc ctcgggcctg aacgacggcg ccgccgcggt ggtggtgatg     780
tcggcggcca aggccaagga actgggcctg accccgctgg ccacgatcaa gagctatgcc     840
aacgccggtg tcgatcccaa ggtgatgggc atgggcccgg tgccggcctc caagcgcgcc     900
ctgtcgcgcg ccgagtggac cccgcaagac ctggacctga tggagatcaa cgaggccttt     960
gccgcgcagg cgctggcggt gcaccagcag atgggctggg acacctccaa ggtcaatgtg    1020
aacggcggcg ccatcgccat cggccacccg atcggcgcgt cgggctgccg tatcctggtg    1080
acgctgctgc acgagatgaa gcgccgtgac gcgaagaagg gcctggcctc gctgtgcatc    1140
ggcggcggca tgggcgtggc gctggcagtc gagcgcaaat ga                      1182
```

<210> SEQ ID NO 21
<211> LENGTH: 284
<212> TYPE: PRT
<213> ORGANISM: C. necator

<400> SEQUENCE: 21

Met Ser Ile Arg Thr Val Gly Ile Val Gly Ala Gly Thr Met Gly Asn
1               5                   10                  15

Gly Ile Ala Gln Ala Cys Ala Val Val Gly Leu Asn Val Val Met Val
            20                  25                  30

Asp Ile Ser Asp Ala Ala Val Gln Lys Gly Val Ala Thr Val Ala Ser
        35                  40                  45

Ser Leu Asp Arg Leu Ile Lys Lys Glu Lys Leu Thr Glu Ala Asp Lys
    50                  55                  60

Ala Ser Ala Leu Ala Arg Ile Lys Gly Ser Thr Ser Tyr Asp Asp Leu
65                  70                  75                  80

Lys Ala Thr Asp Ile Val Ile Glu Ala Thr Glu Asn Tyr Asp Leu
            85                  90                  95

Lys Val Lys Ile Leu Lys Gln Ile Asp Gly Ile Val Gly Glu Asn Val
            100                 105                 110

Ile Ile Ala Ser Asn Thr Ser Ser Ile Ser Ile Thr Lys Leu Ala Ala
            115                 120                 125

Val Thr Ser Arg Ala Asp Arg Phe Ile Gly Met His Phe Asn Pro
130                 135                 140

Val Pro Val Met Ala Leu Val Glu Leu Ile Arg Gly Leu Gln Thr Ser
145                 150                 155                 160

Asp Thr Thr His Ala Ala Val Glu Ala Leu Ser Lys Gln Leu Gly Lys
            165                 170                 175

Tyr Pro Ile Thr Val Lys Asn Ser Pro Gly Phe Val Val Asn Arg Ile
            180                 185                 190

Leu Cys Pro Met Ile Asn Glu Ala Phe Cys Val Leu Gly Glu Gly Leu
            195                 200                 205

Ala Ser Pro Glu Glu Ile Asp Glu Gly Met Lys Leu Gly Cys Asn His
            210                 215                 220

Pro Ile Gly Pro Leu Ala Leu Ala Asp Met Ile Gly Leu Asp Thr Met
225                 230                 235                 240

Leu Ala Val Met Glu Val Leu Tyr Thr Glu Phe Ala Asp Pro Lys Tyr
                245                 250                 255

Arg Pro Ala Met Leu Met Arg Glu Met Val Ala Ala Gly Tyr Leu Gly
            260                 265                 270

Arg Lys Thr Gly Arg Gly Val Tyr Val Tyr Ser Lys
            275                 280

<210> SEQ ID NO 22
<211> LENGTH: 855
<212> TYPE: DNA
<213> ORGANISM: Artificial sequence
<220> FEATURE:
<223> OTHER INFORMATION: Synthetic

<400> SEQUENCE: 22
atgagcatcc gcaccgtggg catcgtcggt gccggcacaa tgggcaacgg catcgcgcag    60
gcctgcgcgg tggtcggcct gaatgtcgtg atggtggata tcagcgacgc cgccgtgcaa   120
aagggcgtgg ccaccgtggc ctcgtccctg accgtctga ttaagaagga aaagctgacc   180
gaggccgaca aggcctcggc cctcgcgcgc atcaagggca gcacgtcgta tgatgacctg   240
aaggcgaccg acatcgtgat cgaagcggcc accgagaact acgacctgaa ggtgaagatc   300
ctgaagcaaa tcgacggtat cgtcggcgaa aacgtcatca tcgcctcgaa cacgagctcc   360
atcagcatca ccaagctcgc cgccgtgacc tcgggcggg accgcttcat cggcatgcat   420
ttcttcaacc cggtcccggt gatggccctc gtcgaactga tccgcggcct ccagacctcg   480
gatacgacgc acgcggcggt cgaagccctc agcaagcagc tgggcaagta ccccatcacc   540
gtgaagaact cgccgggctt cgtggtcaat cgcatcctct gccccatgat caacgaagcg   600
ttttgcgtcc tgggcgaggg cctggcgtcc ccgaagaga ttgacgaagg catgaagctg   660
ggctgcaacc acccgatcgg cccgctggcg ctggccgata tgatcggcct ggacacgatg   720
ctggcggtga tggaagtgct gtacaccgag ttcgcggacc ccaagtaccg tccggcgatg   780

```
ctgatgcgcg agatggtggc ggccggctat ctgggccgca agacgggtcg cggcgtgtat    840
gtgtacagca agtga                                                    855
```

<210> SEQ ID NO 23
<211> LENGTH: 282
<212> TYPE: PRT
<213> ORGANISM: Clostridium acetobutylicum

<400> SEQUENCE: 23

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280
```

<210> SEQ ID NO 24
<211> LENGTH: 849
<212> TYPE: DNA
<213> ORGANISM: Artificial sequence
<220> FEATURE:
<223> OTHER INFORMATION: Synthetic

<400> SEQUENCE: 24

```
atgaagaagg tgtgcgtgat cggcgccggc acgatgggct ccggtatcgc ccaggcgttc    60
gccgcgaagg gcttcgaggt cgtcctgcgg gacatcaagg acgagttcgt ggaccgcggt   120
```

```
ctggactttta tcaataagaa cctgagcaag ctcgtgaaga agggcaagat tgaagaagcc    180
accaaggtcg agatcctgac gcgcatcagc ggcaccgtgg atctgaacat ggcggccgac    240
tgcgatctgg tgatcgaggc cgccgtcgag cgcatggata tcaagaagca aatcttcgcc    300
gacctcgaca catctgcaa gccggaaacc atcctggcga gcaacacgtc gtcgctgtcg    360
attaccgaag tggcgagcgc caccaagcgg cccgacaagg tcatcggcat gcacttcttc    420
aacccggccc cggtgatgaa gctcgtcgag gtgatccgcg catcgcgac agccaggaa     480 acgttcgacg cggtgaagga acctccatc gcgatcggca aggacccggt cgaggtcgcc    540
gaggcccccg gctttgtggt gaaccgcatc ctgatcccca tgatcaacga agcggtgggc    600
atcctggccg agggcatcgc ctcggtcgaa gatatcgaca aggccatgaa gctgggcgcg    660
aatcacccga tgggcccgct ggagctgggc gacttcatcg gcctggacat ctgcctcgcc    720
attatggacg tgctgtactc ggaaacgggc gactcgaagt atcgcccgca tacctgctg    780 aagaagtacg tgcgcgcggg ctggctgggt cgtaagtccg gcaagggctt ctacgactac    840
agcaagtga                                                           849
```

<210> SEQ ID NO 25
<211> LENGTH: 246
<212> TYPE: PRT
<213> ORGANISM: C. necator

<400> SEQUENCE: 25

```
Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240
```

```
Gly Gly Leu His Met Gly
                    245

<210> SEQ ID NO 26
<211> LENGTH: 741
<212> TYPE: DNA
<213> ORGANISM: Artificial sequence
<220> FEATURE:
<223> OTHER INFORMATION: Synthetic

<400> SEQUENCE: 26
atgacgcagc gcattgcgta tgtcacgggc ggcatgggcg gcatcggcac cgccatctgc      60
cagcgcctgg cgaaggacgg cttccgcgtg gtggccggct gcggcoccaa ctccccgcgc     120 cgtgaaaagt ggctggagca gcaaaaggcc ctcggcttcg atttcatcgc gagcgagggc     180
aacgtcgccg actgggactc gaccaagacc gccttcgaca aggtcaagtc ggaagtcggc     240
gaggtcgatg tgctcatcaa taatgccggc atcacccgtg acgtggtgtt ccggaagatg     300
acccgcgcgg actgggacgc ggtgattgac accaacctga cctccctgtt caacgtcacc     360
aagcaagtca tcgacggcat ggcggatcgc ggctggggcc gcatcgtgaa catcagcagc     420
gtcaacggcc agaagggtca gttcggtcag accaactact cgaccgccaa ggccggcctg     480
cacggcttta caatggccct cgcgcaagaa gtggcgacca agggcgtcac cgtgaacacg     540
gtgagccccg gttacatcgc gacggacatg gtgaaggcca tccgccaaga cgtgctggat     600
aagatcgtcg ccacgatccc ggtgaagcgc ctgggcctgc cggaagagat cgcctccatc     660
tgcgcctggc tgtcgtcgga agagtcgggc ttcagcaccg gcgcggactt ctcgctgaac     720
ggcggcctgc acatgggctg a                                               741
```